United States Patent
Cheng et al.

(10) Patent No.: US 7,105,556 B2
(45) Date of Patent: Sep. 12, 2006

(54) CONFORMATIONALLY CONSTRAINED ANALOGS USEFUL AS ANTIDIABETIC AND ANTIOBESITY AGENTS AND METHOD

(75) Inventors: Peter T. Cheng, Princeton, NJ (US); Yoon Jeon, Belle Mead, NJ (US); Wei Wang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 478 days.

(21) Appl. No.: 10/153,342

(22) Filed: May 22, 2002

(65) Prior Publication Data
US 2003/0092697 A1 May 15, 2003

Related U.S. Application Data

(60) Provisional application No. 60/294,505, filed on May 30, 2001.

(51) Int. Cl.
- *A61P 3/04* (2006.01)
- *A61K 31/42* (2006.01)
- *A61K 31/445* (2006.01)
- *A61K 31/55* (2006.01)
- *C07D 403/02* (2006.01)

(52) U.S. Cl. .......... 514/374; 514/89; 514/91; 514/92; 514/93; 514/94; 514/217.03; 514/217.04; 514/217.08; 514/217.09; 514/318; 514/326; 514/333; 514/340; 514/341; 514/342; 514/343; 514/360; 514/361; 514/362; 514/363; 514/364; 514/365; 514/369; 514/372; 514/376; 514/378; 514/380; 514/381; 514/397; 514/406; 514/407; 514/422; 514/423; 514/428; 540/596; 540/597; 540/602; 540/603; 546/22; 546/24; 546/193; 546/194; 546/208; 546/209; 546/210; 546/211; 546/256; 546/268.4; 546/268.7; 546/269.1; 546/269.4; 546/269.7; 546/270.4; 546/271.1; 546/271.4; 546/272.1; 546/272.7; 546/274.1; 546/274.4; 546/275.1; 546/275.4; 546/276.1; 546/276.4; 546/278.4; 546/279.1; 548/111; 548/119; 548/122; 548/123; 548/124; 548/125; 548/127; 548/134; 548/135; 548/182; 548/187; 548/203; 548/204; 548/206; 548/213; 548/214; 548/225; 548/228; 548/235; 548/236; 548/240; 548/243; 548/247; 548/248; 548/255; 548/314.7; 548/364.1; 548/412

(58) Field of Classification Search ............... 514/374; 548/236
See application file for complete search history.

(56) References Cited

FOREIGN PATENT DOCUMENTS

| | | |
|---|---|---|
| GB | 2 027 025 A | 7/1979 |
| WO | WO 93/01167 | 3/1992 |
| WO | WO 01/38325 A1 | 11/2000 |
| WO | WO 01/21602 A1 | 3/2001 |

OTHER PUBLICATIONS

Davis, Franklin A., et al., Organic Letters, 2001, vol. 3, No. 5, 759-762.
Swarbrick, Martin E., J. Org. Chem. 1999, 64, 1993-2002.
Jeff E. Cobb, et al., "N-(2-Benzoylphenyl)-L-tyrosine PPARγ Agonist 3 Structure-Activity Relationship and Optimization of the N-Aryl Substituent", J. Med. Chem., 1998, 41, 5055-5069.

*Primary Examiner*—Brenda Coleman
(74) *Attorney, Agent, or Firm*—Burtin Rodney

(57) ABSTRACT

Compounds are provided which have the structure

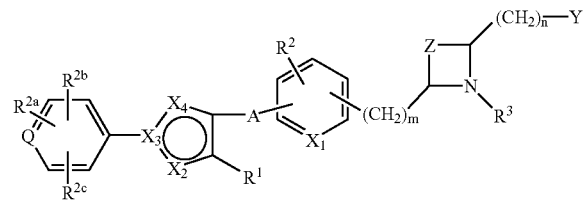

wherein Q is C or N, $X_1$ is C or N, and $R^1$, $R^2$, $R^{2a}$, $R^{2b}$, $R^{2c}$, $R^3$, Y, A, m, n, $X_2$, $X_3$ and $X_4$ are as defined herein, which compounds are useful as antidiabetic, hypolipidemic, and antiobesity agents.

17 Claims, No Drawings

CONFORMATIONALLY CONSTRAINED ANALOGS USEFUL AS ANTIDIABETIC AND ANTIOBESITY AGENTS AND METHOD

This application claims priority from U.S. provisional application No. 60/294,505 filed May 30, 2001 which is incorporated herein by reference.

FIELD OF THE INVENTION

The present invention relates to novel substituted azole acid derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted acid derivatives alone or in combination with another antidiabetic agent and/or a hypolipidemic agent and/or other therapeutic agents.

DESCRIPTION OF THE INVENTION

In accordance with the present invention, substituted acid derivatives are provided which have the structure I

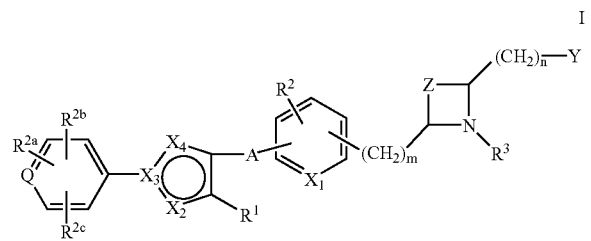

wherein m is 0, 1 or 2; n=0, 1 or 2;

Q is C or N;

A is $(CH_2)_x$ where x is 1 to 5; or A is $(CH_2)_x^1$, where $x^1$ is 2 to 5, with an alkenyl bond or an alkynyl bond embedded anywhere in the chain; or A is $-(CH_2)_x^2-O-(CH_2)_x^3-$ where $x^2$ is 0 to 5 and $x^3$ is 0 to 5, provided that at least one of $x^2$ and $x^3$ is other than 0;

$X_1$ is CH or N;

$X_2$ is C, N, O or S;

$X_3$ is C or N;

$X_4$ is C, N, O or S, provided that at least one of $X_2$, $X_3$ and $X_4$ is N.

In each of $X_1$ through $X_4$, as defined above, C may include CH.

$R^1$ is H or alkyl;

$R^2$ is H, alkyl, alkoxy, halogen, amino or substituted amino;

$R^{2a}$, $R^{2b}$ and $R^{2c}$ may be the same or different and are selected from H, alkyl, alkoxy, halogen, amino or substituted amino;

$R^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylarylalkyl;

Y is $CO_2R^4$ (where $R^4$ is H or alkyl, or a prodrug ester) or Y is a C-linked 1-tetrazole, a phosphinic acid of the structure $P(O)(OR^{4a})R^5$ (where $R^{4a}$ is H or a prodrug ester, $R^5$ is alkyl or aryl) or a phosphonic acid of the structure $P(O)(OR^{4a})_2$;

Z is $(CH_2)_x^4$ where $x^4$ is 1 to 5 (preferably 1 to 3); or Z is $(CH_2)_x^5$ where $x^5$ is 2 to 5 (preferably 2 or 3), where $(CH_2)_x^5$ includes an alkenyl (C=C) bond embedded within the chain or Z is $-(CH_2)_x^6-O-(CH_2)_x^7-$ where $x^6$ is 0 to 4 (preferably 1 to 3) and $X^7$ is 0 to 4 (preferably 0 to 2), provided that at least one of $x^6$ and $x^7$ is other than 0;

$(CH_2)_x$, $(CH_2)_x^1$, $(CH_2)_x^2$, $(CH_2)_x^3$, $(CH_2)_x^4$, $(CH_2)_x^5$, $(CH_2)_x^6$, $(CH_2)_x^7$, $(CH_2)_m$, and $(CH_2)_n$ may be optionally substituted with 1, 2 or 3 substituents;

including all stereoisomers thereof, prodrug esters thereof, and pharmaceutically acceptable salts thereof.

Preferred are compounds of formula I of the invention having the structure

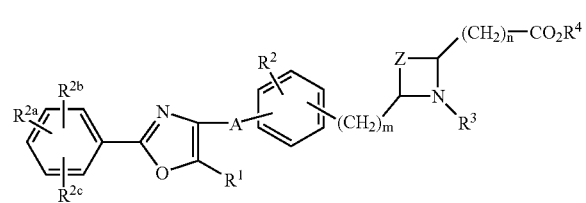

IA where $R^{2a}$, $R^{2b}$ and $R^{2c}$ are each H, $R^1$ is lower alkyl, preferably $CH_3$, A is $(CH_2)_x^1$, where $x^1$ is 2 to 5, with an alkenyl bond or an alkynyl bond embedded anywhere in the chain; or A is $-(CH_2)_x^2-O-(CH_2)_x^3-$ where $x^2$ is 0, 1 or 2, and $x^3$ is 0, m is 0 or 1, Z is $(CH_2)x^4$ where $x^4$ is 2 or 3 or Z is $(CH_2)x^5$ where $x^5$ is 2, 3 or 4 and $(CH_2)x^5$ includes a double bond, n is 0, and $R^3$ is arylalkyl, aryloxycarbonyl, arylalkyloxycarbonyl, with more preferred being alkoxyaryloxycarbonyl or phenoxyarylalkyl.

Preferred compounds of the invention include the following:

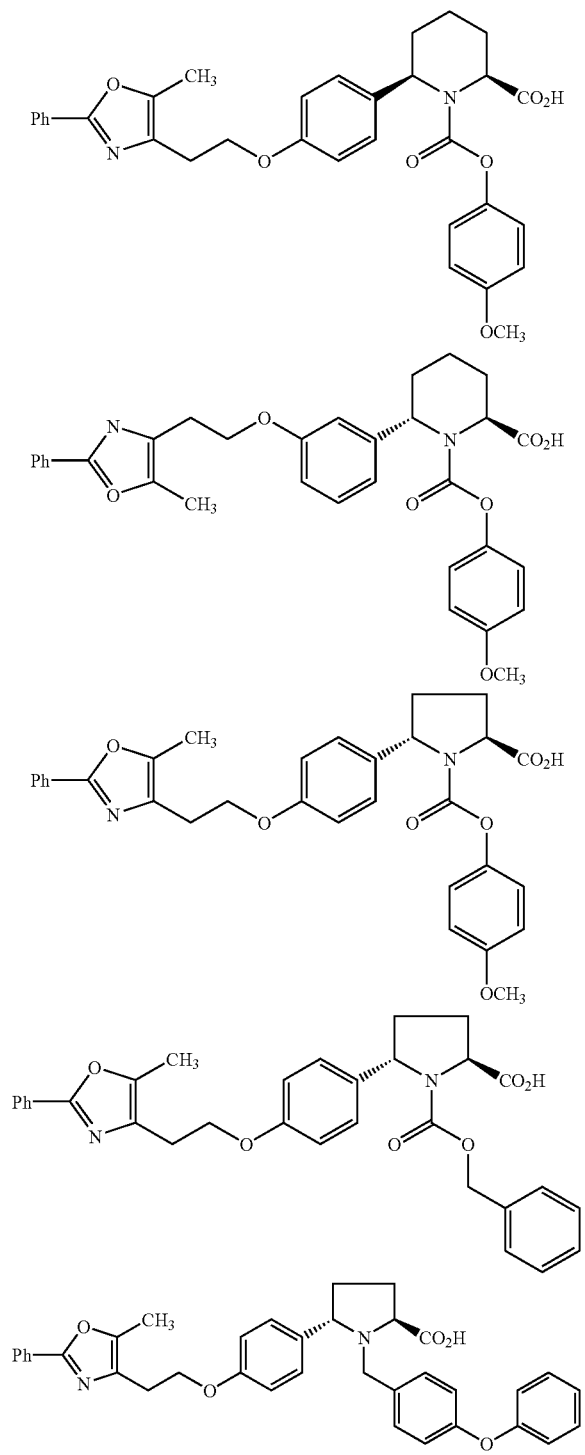

In addition, in accordance with the present invention, a method is provided for treating diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis, and related diseases wherein a therapeutically effective amount of a compound of structure I is administered to a patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of structure I is administered to a patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a patient in need of treatment.

In the above method of the invention, the compound of structure I will be employed in a weight ratio to the antidiabetic agent (depending upon its mode of operation) within the range from about 0.01:1 to about 100:1, preferably from about 0.5:1 to about 10:1.

The conditions, diseases, and maladies collectively referenced to as "Syndrome X" or Dysmetabolic Syndrome (as detailed in Johanson, *J. Clin. Endocrinol. Metab.*, 1997, 82, 727–734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

DETAILED DESCRIPTION OF THE INVENTION

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, Protecting Groups in Organic Synthesis, 3$^{rd}$ Edition, 1999 [Wiley]).

The synthesis of some key intermediates required for the synthesis of the compounds in this patent are described in Scheme 1. An alcohol 1 ($R^5(CH_2)_x{}^2OH$) (of which one of the most preferred is 2-phenyl-5-methyl-oxazole-4-ethanol) is coupled with a hydroxy aryl- or heteroaryl-aldehyde 2 under standard Mitsunobu reaction conditions (e.g. Mitsunobu, O., *Synthesis*, 1981, 1) to furnish the key intermediate aldehyde 3. Alternatively, the alcohol 1 can be converted to its methanesulfonate ester 4 under standard conditions; the mesylate 4 can then be used to alkylate the hydroxy aryl- or heteroaryl-aldehyde 2 to furnish the aldehyde 3.

Scheme 2 describes a synthesis of the proline analogs IB of the invention. A protected hydroxyaryl- or hydroxyheteroaryl-methyl ketone 5 undergoes a Mannich reaction with an amine such as N-methyl morpholine and paraformaldehyde (e.g. Kato, E. et al, *Chem. Pharm. Bull*, 1985, 33, 4836) to provide the β-aminoketone 6. Quaternization of the aminoketone 6 followed by displacement with an appropriately protected amino-malonate 7 under appropriate basic conditions gives the keto-amino-malonate 8 (Kato, E. et al, *Chem. Pharm. Bull*, 1985, 33, 4836). Deprotection of the phenol of amino-malonate 8 provides the phenol 9, which is then reacted with the preferred alcohol 1 under standard Mitsunobu conditions to furnish the alkylated phenol 10. Acid-mediated deprotection of both the amine and the carboxylic acid followed by decarboxylation with concomitant internal cyclization of the amino-ketone provides the key intermediate imino-acid 11 (Kato, E. et al, *Chem. Pharm. Bull*, 1985, 33, 4836). Reduction of the imine under standard conditions (e.g. Abdel-Magid, A. F., et al, *J. Org. Chem.*, 1996, 61, 3849) provides the corresponding 5-substituted proline analogs IB of the invention.

As shown in Scheme 3, the amino acid I then can be reacted with an appropriate chloroformate 12 under standard Schotten-Baumann conditions to provide the carbamate-substituted proline analogs II of the invention. Alternatively, amino acid I can undergo reductive amination under standard conditions (Abdel-Magid, A. F., et al, *J. Org. Chem.*, 1996, 61, 3849) with an appropriate aldehyde 13 to furnish the N-substituted amino acid analog III of the invention.

An asymmetric synthesis of cyclic amino acids IV and V is shown in Schemes 4 and 5. A protected hydroxyaryl- or hydroxy-heteroaryl-halide 14 is metalated with an appropriate lithiating agent (e.g. tert-butyllithium or n-butyllithium) to give the corresponding aryl- or heteroaryllithium reagent 15. The appropriately protected chiral Weinreb amide 16 (with the preferred PG$_2$ being tert-butyl) is prepared in one step by coupling the corresponding chiral bis-protected amino-diacid with N-methoxy N-methyl amine under standard literature conditions (e.g. Rapopprt, H. et al, *J. Org. Chem.* 1996, 61, 715–721). The aryl- or heteroaryllithium reagent 15 is reacted with the Weinreb amide 16 to furnish the chiral protected keto-amino acid 17. Deprotection of the phenol functionality of the keto-amino acid 17 furnishes the phenol 18. This is then followed by alkylation of phenol 18 with the preferred alcohol 1 under standard Mitsunobu conditions to provide the alkylated phenol 19. Asymmetric reduction of the ketone functionality of the protected amino acid 19 under standard literature conditions (Corey, E. J., et al, *Angew. Chem. Int. Ed.*, 1998, 37, 1986) provides the diastereomerically pure hydroxy protected amino-acid 20. It is understood that the conditions/reagents of the reduction can be changed such that either diastereomer can be obtained. Conversion of the hydroxyl group of 20 to a leaving group (such as methanesulfonate) followed by treatment with base furnishes the protected chiral cyclic amino acid 21. Selective deprotection of the amine functionality of 21 provides the amino acid intermediate 22. This amine 22 can then be reacted with appropriate chloroformates followed by deprotection of the carboxylic acid functionality to provide the chiral cyclic carbamate-acid IV of the invention. Alternatively, a protected chiral amino acid 22 can undergo reductive amination under standard conditions (Abdel-Magid, A. F., et al, *J. Org. Chem.*, 1996, 61, 3849) with appropriate aldehyde 13 to furnish the chiral N-alkyl cyclic amino acid analog V of the invention.

Alternatively, as shown in Scheme 6, cyclic amino acids VI and VII can be synthesized in a different manner starting from the bis-protected keto-amino acid 19. Acid-mediated deprotection of the amine followed by internal cyclization (imine formation) furnishes the protected imino-acid 23 (e.g. Ezquerra, J., et al, *Tetrahedron Lett.*, 1993, 34, 6317). Stereoselective imine reduction then furnishes the protected amino acid 24. Amino acid intermediate 24 then can be reacted with appropriate chloroformates, followed by deprotection of the carboxylic acid to furnish cyclic carbamate-acid analog VI of the invention. Alternatively, amino acid intermediate 24 can be reacted with an appropriate aldehyde 13 under reductive amination conditions, followed by deprotection of the carboxylic acid to furnish N-alkylated cyclic amino acid analog VII of the invention.

Scheme 7 shows a third general method for the synthesis of cyclic acid analogs. The substituted alkylated hydroxyaryl or heteroaryl-aldehyde 3 is reacted with an appropriately protected amino acid 26 (which contains a terminal alkene in the α-side-chain) to furnish the protected imino-acid 27 (e. g. Loh, T. P., et al, *Tetrahedron Lett.*, 1993, 34, 6317). The imine 27 is then reacted with an alkenyl-substituted halide in the presence of an appropriate transition metal (preferably indium) to provide the key bis-alkenyl amino acid intermediate 29 (Loh, T. P., et al, *Tetrahedron Lett.*, 1993, 34, 6317). The amine functionality of 29 is appropriately protected and this intermediate is then subjected to olefin metathesis according to standard literature conditions (review: Furstner, A., *Angew. Chem. Int. Ed.*, 2000, 39, 3012) to provide the cyclized cycloalkene 30. The amine functionality of the amino-acid intermediate 30 is then deprotected to give the amino-ester 31. Amino-ester 31 can then be reacted with an appropriate chloroformate 12, followed by deprotection of the carboxylic acid to furnish cyclic carbamate-acid analog VIII of the invention. Alternatively, amino acid intermediate 31 can be reacted with an appropriate aldehyde 13 under reductive amination conditions, followed by deprotection of the carboxylic acid to furnish N-alkylated cyclic amino acid analog IX of the invention.

Scheme 8 shows a method for preparing cyclic alkenyl carbamate-acid analog X wherein the amino acid intermediate 31 is reacted with an appropriate chloroformate 12, followed by hydrogenation (e.g. with $H_2/Pd/C$), followed by deprotection to form cyclic carbamate-acid analog X of the invention. Alternatively, the amino acid intermediate 31 can be reacted with an appropriate aldehyde 13 under standard reductive amination conditions, followed by hydrogenation and deprotection of the carboxylic acid to furnish N-alkylated cyclic amino acid analog XI of the invention.

Scheme 9 shows shows the preparation of the required intermediate 2-aryl (or heteroaryl)-5-methyl-oxazol4-yl mesylate 37 (following the general procedure described in Malamas, M. S., et al, *J. Med. Chem.*, 1996, 39, 237–245). A substituted aryl aldehyde 32 is condensed with butane-2,3-dione mono-oxime under acidic conditions to give the corresponding oxazole N-oxide 33. Deoxygenation of the oxazole N-oxide 33 with concomitant chlorination furnishes the desired chloromethyl aryl (or heteroaryl)-oxazoles 34. Hydrolysis of chloromethyl oxazole 34 under basic conditions furnishes the corresponding oxazole-methanol 35. Oxidation of alcohol 35 to the corresponding aldehyde is followed by conversion to the corresponding dibromoalkene 36 (e.g. $Ph_3P/CBr_4$). The dibromide 36 is converted to the corresponding alkynyl-lithium species (using an organo-lithium reagent such as n-BuLi), which can be reacted in situ with an appropriate electrophile such as formaldehyde to give the corresponding acetylenic alcohol (ref: Corey, E. J., et al., *Tetrahedron Lett.* 1972, 3769, or Gangakhedkar, K. K., *Synth. Commun.* 1996, 26, 1887–1896). This alcohol can then be converted to the corresponding mesylate 37.

Scheme 10 illustrates the synthesis of alkenyl and alkynyl-linked analogs of the invention. Asymmetric reduction of the ketone functionality of the protected amino acid 17 under standard literature conditions (Corey, E. J., et al, *Angew. Chem. Int. Ed.*, 1998, 37, 1986) provides the diastereomerically pure hydroxy protected amino-acid 38. It is understood that the conditions/reagents of the reduction can be changed such that either diastereomer can be obtained. Conversion of the hydroxyl group of 38 to a leaving group (such as methanesulfonate) followed by treatment with base (such as triethylamine) furnishes the protected chiral cyclic amino acid 39. Selective deprotection of the amine functionality of 39 (such as treating with HCl in $CH_3OH$ where $PG_3$ is BOC) provides the amino acid intermediate 40. This amine 40 can then undergo the following sequence: 1) reaction with an appropriate chloroformate 12, 2) selective deprotection of the phenol, 3) alkylation with mesylate 37 and 4) deprotection of the carboxylic acid to furnish the alkyne-acid analog XII of the invention. Stereoselective partial reduction of alkyne XII of the invention (e.g. $H_2$/Lindlar's catalyst) provides the E- or Z-alkenyl analogs XIII of the invention. Complete reduction of alkene analogs XIII (e.g. $H_2$/Pd/C) provides the alkyl analogs XIV of the invention. Alternatively, complete reduction (e.g. $H_2$/Pd/C) of alkyne analogs XII of the invention also provides the alkyl analogs XIV of the invention.

The synthesis of carbon-linked analogs XV, XVI, and XVII are shown in Scheme 11. Treatment of the protected amine intermediate 40 with an appropriate chloroformate 12, followed by selective deprotection of the phenol and subsequent reaction with triflic anhydride in the presence of base provides the aryl triflate 41. Coupling of the alkyne 42 with aryl triflate 41 under standard Sonogashira reaction conditions (e.g. "Organocopper Reagents, a Practical Approach", R. J. K. Taylor, E., Chapter, 10, p 217–236, Campbell, I. B., Oxford University Press, 1994) furnishes the corresponding alkynye, which then undergoes deprotection to give alknyl acid analogs XV of the invention. Selective reduction of the alkynyl acid XV of the invention (e.g. $H_2$/Lindlar catalyst) provides the E- or Z-alkenyl acids XVI of the invention. Complete reduction of alkenyl acids XVI (hydrogenation) of the invention then provides the saturated alkyl acids XVII of the invention.

The syntheses of the homologated ether-containing analogs XVIII–XXII are shown in Schemes 12–14.

In Scheme 12, carbonylation of the aryl triflate 41 with carbon monoxide in the presence of a suitable palladium catalyst such as palladium (II) acetate and a base such as triethylamine (ref: *Synth. Commun.* 1998, 28, 4279–4285) followed by reduction (e.g. $NaBH_4$) provides the aryl alcohol 43. Treatment of alcohol 43 with mesylate 4 in the presence of base provides the corresponding ether-carbamate ester, which is then deprotected to furnish the ether-carbamate acid XVIII of the invention.

In Scheme 13, coupling of aryl triflate 41 with an appropriate vinyl tin reagent (e.g. tributylvinyltin) under Stille coupling conditions (reference: Farina, V., Krishnamurthy, V., and Scott, W. J., *Organic Reactions*, 1997, 50, 1; also *Tetrahedron Lett.*, 1998, 39, 9513) provides the corresponding aryl-vinyl intermediate, which then undergoes hydroboration (e.g. borane-THF, then $H_2O_2$) to give the aryl alcohol 44. Treatment of alcohol 44 with mesylate 4 in the presence of an appropriate base provides the corresponding ether-carbamate ester, which is then deprotected to provide the ether-carbamate acid XIX of the invention.

A synthesis of other ether-linked carbamate acids XX–XII is shown in Scheme 14. Reaction of a suitably protected acetylenic alcohol 45 (where $x^3$=1–3 is preferred) under standard Sonogashira coupling conditions (e.g. "Organocopper Reagents, a Practical Approach", R. J. K. Taylor, E., Chapter, 10, p 217–236, Campbell, I. B., Oxford University Press, 1994; also *J. Org. Chem.*, 2000, 65, 1780) furnishes the corresponding alkynyl carbamate-ester. Removal of the alcohol protecting group then furnishes the alcohol 46. Treatment of alcohol 46 with mesylate 4 in the presence of base provides the corresponding alkynyl ether-carbamate ester, which is then deprotected to furnish the alkynyl ether-acid XX of the invention. Stereoelective hydrogenation (e.g. Lindlar's catalyst) of alkynyl-acid XX then furnishes alkenyl-acid XXI of the invention. Complete hydrogenation (e.g. $H_2$/Pd/C) of alkenyl-acid XXI then provides the alkyl-acid XXII of the invention.

SCHEME 1

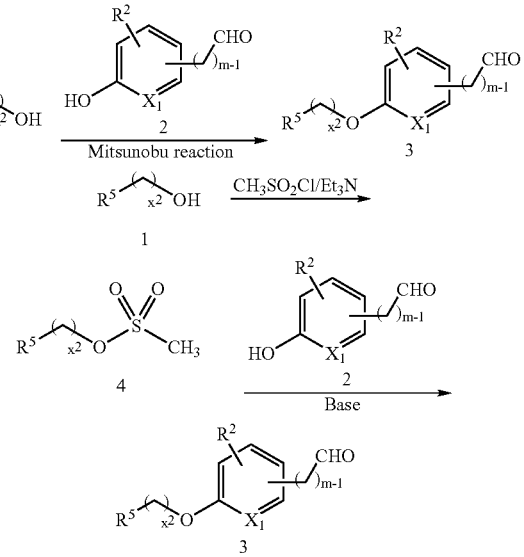

In this and the following Reaction Schemes, $R^5$ =
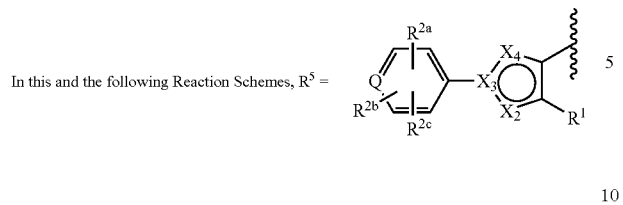
SCHEME 2
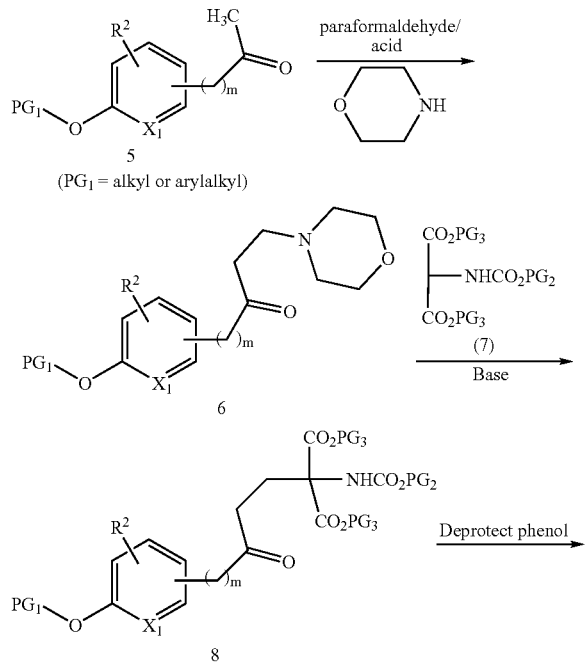
(PG$_1$ = alkyl or arylalkyl)
(PG$_2$ = alkyl or arylalkyl
PG$_3$ = alkyl or arylalkyl)
-continued
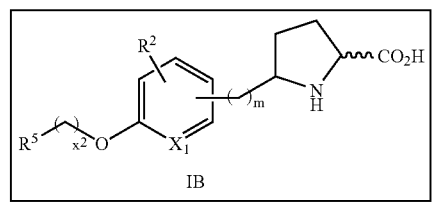
SCHEME 3
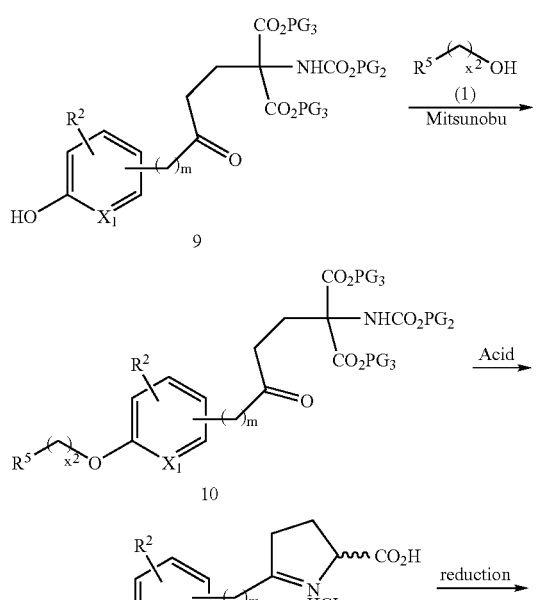
($R^{3a}$ can be any of the $R^3$ groups such as alkyl, aryl or heteroaryl)
SCHEME 4
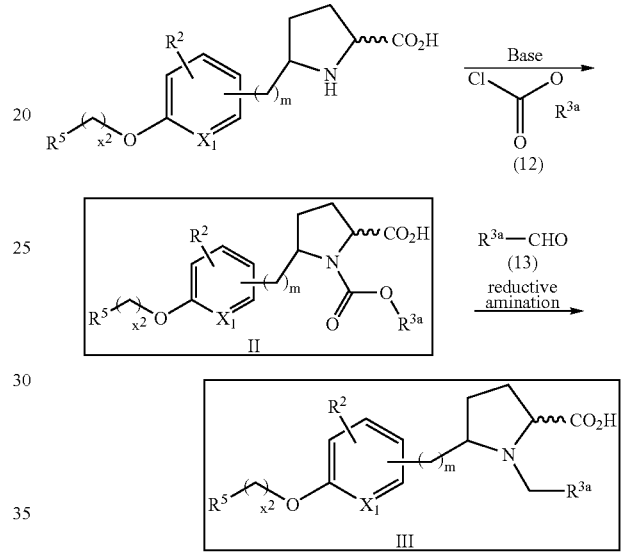
(PG$_2$ is alkyl or arylalkyl
PG$_3$ is CO$_2$-alkyl or CO$_2$-arylalkyl)
($x^8$ = 1 to 4)

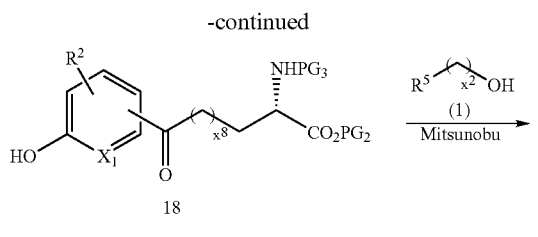
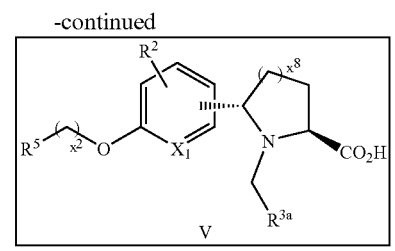
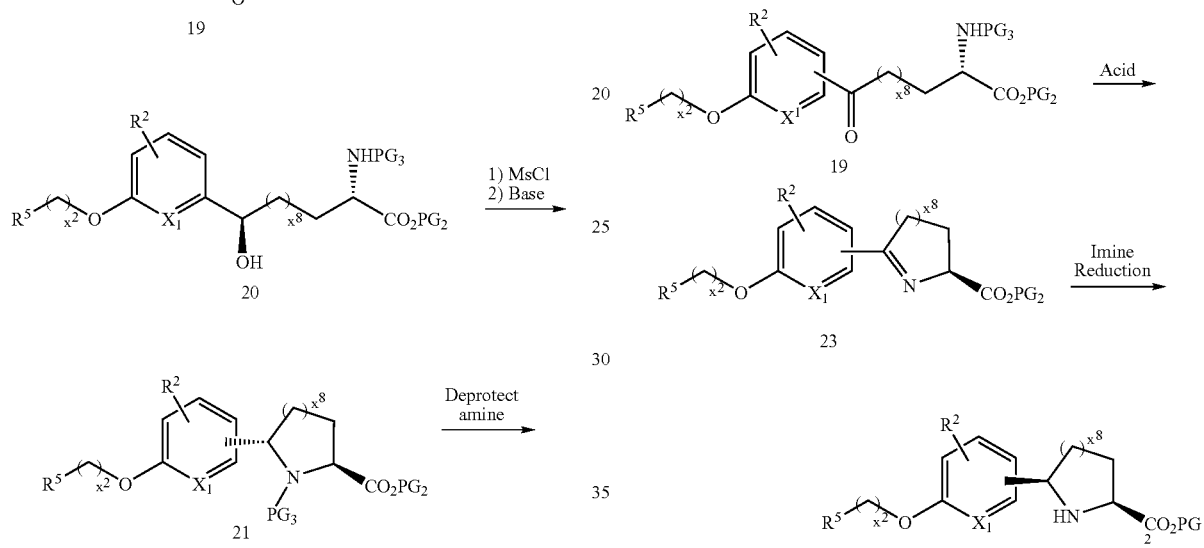
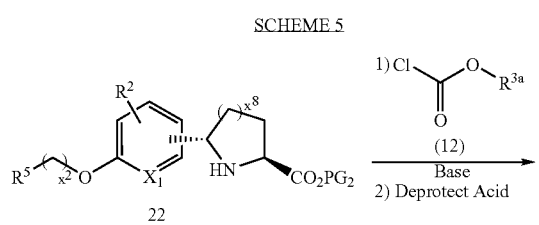
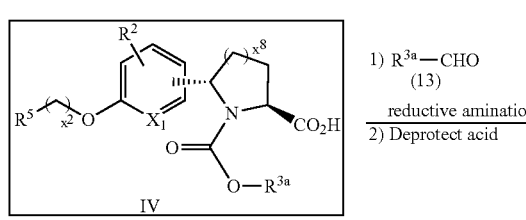

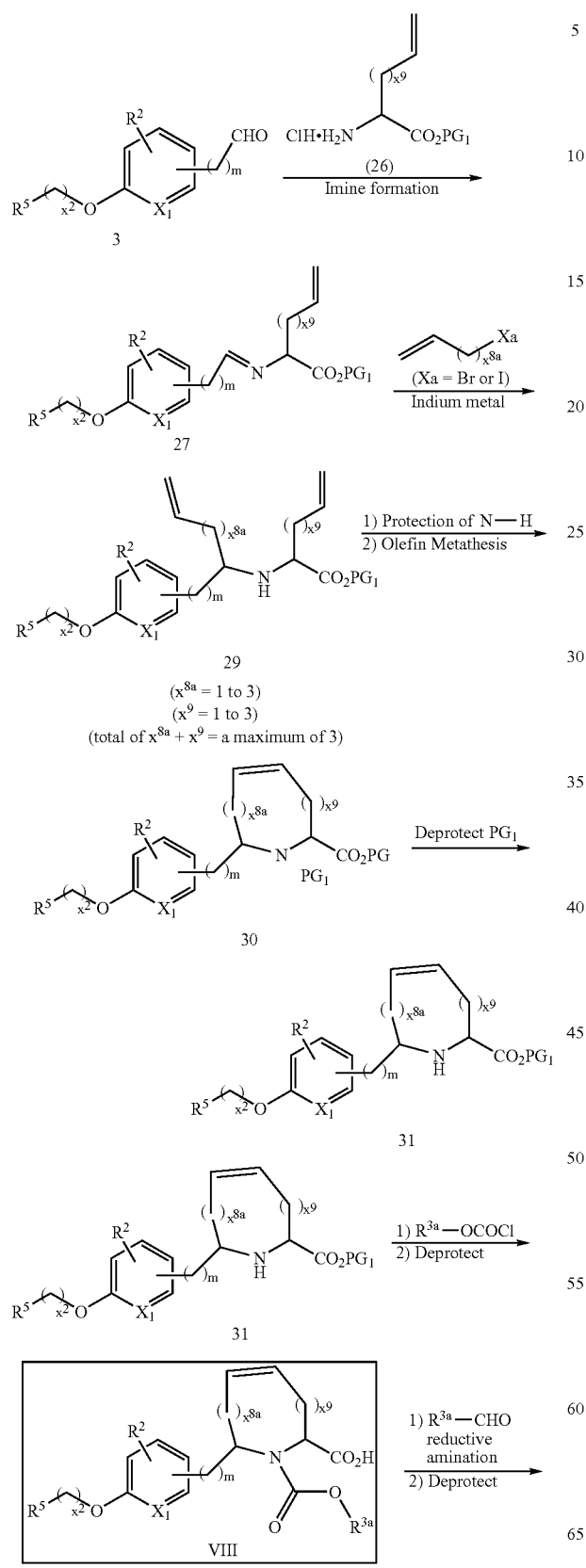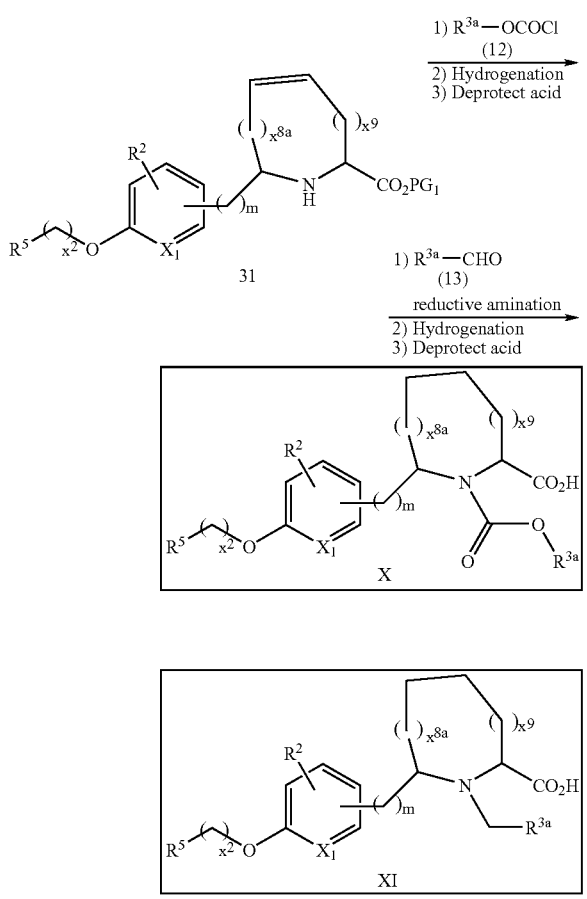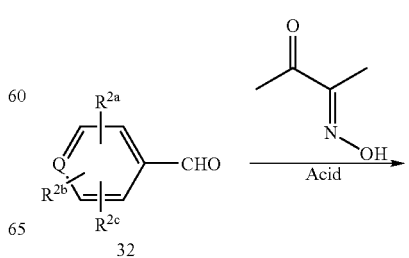

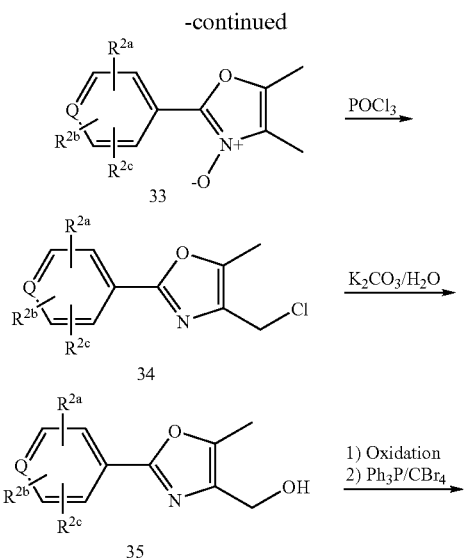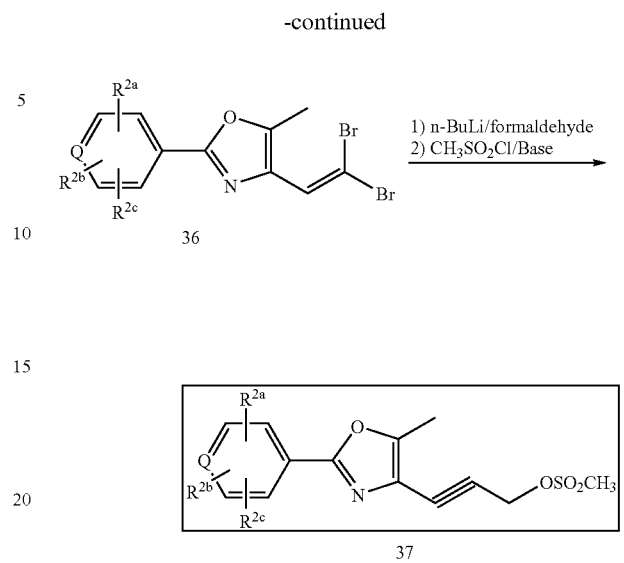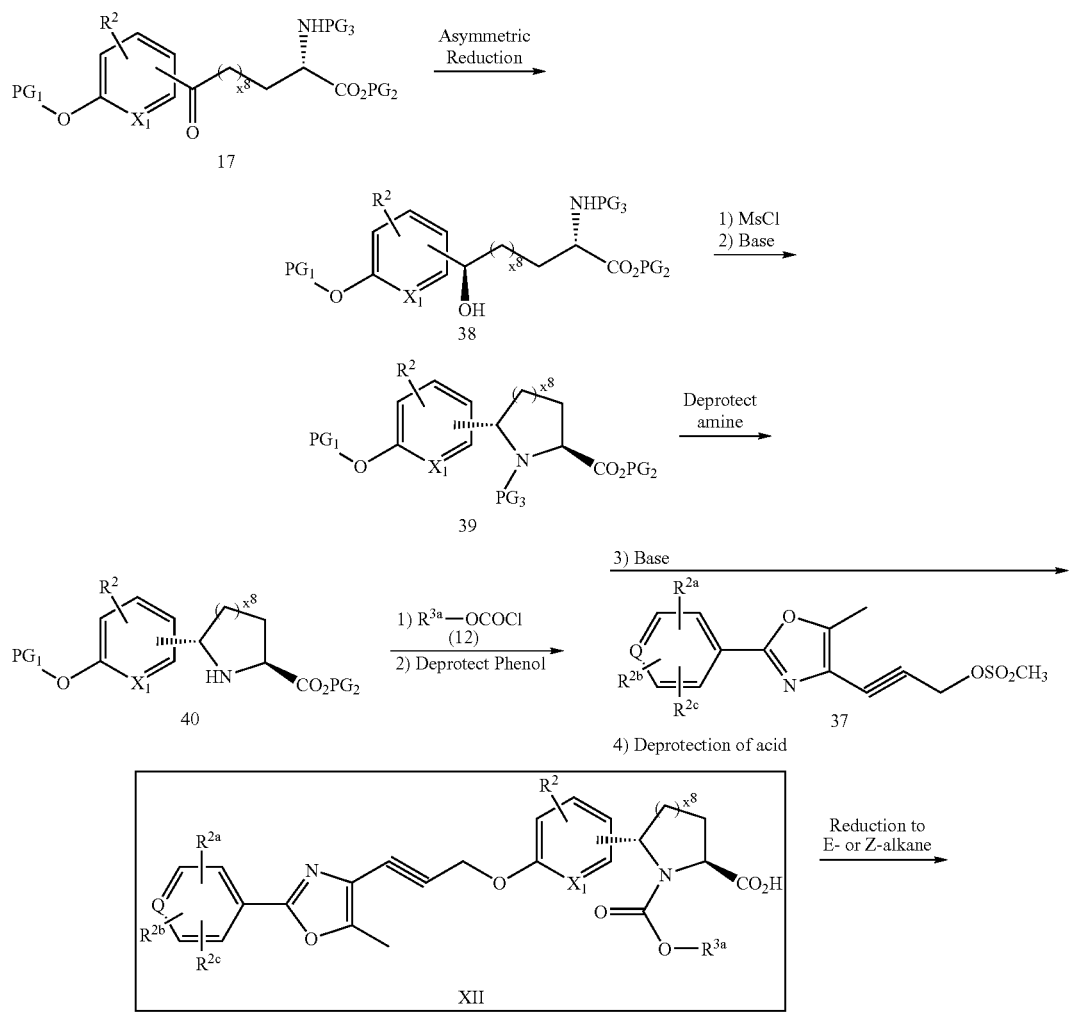

-continued

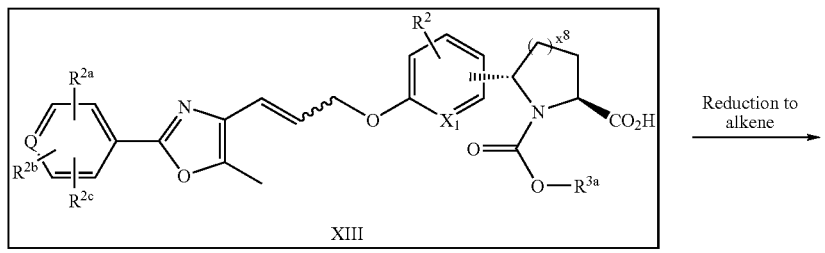

XIII

Reduction to alkene →

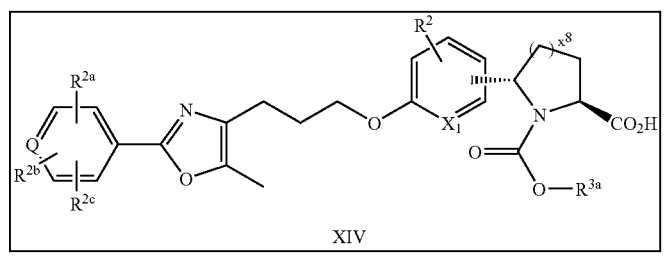

XIV

SCHEME 11

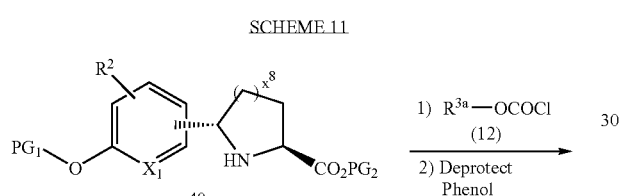

40

1) R³ᵃ—OCOCl (12)
2) Deprotect Phenol
3) (Tf)₂O/Base

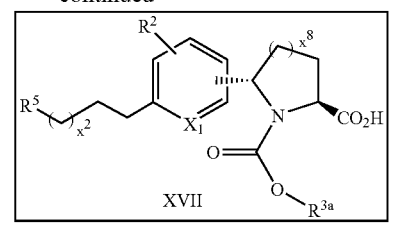

XVII

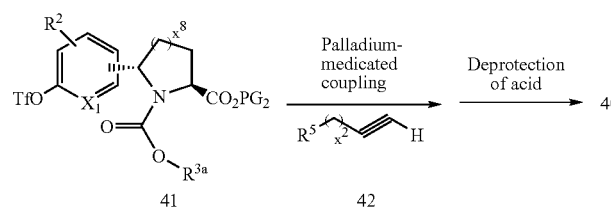

41

Palladium-medicated coupling $R^5\!-\!\!\!\equiv\!\!\!-\!H$ (x²)
42

Deprotection of acid

-continued

SCHEME 12

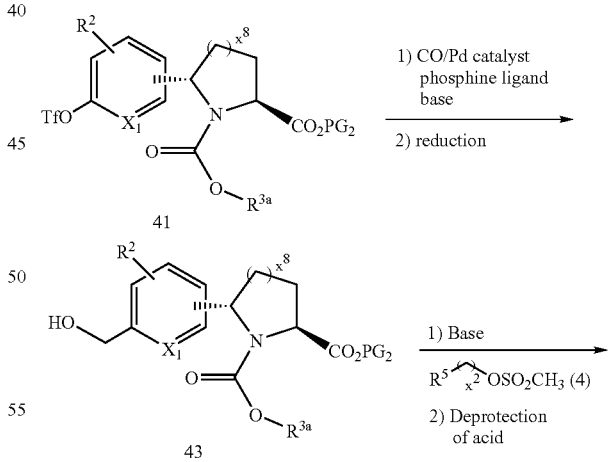

41

1) CO/Pd catalyst phosphine ligand base
2) reduction

43

1) Base
   $R^5\!-\!\!(x^2)\!-\!OSO_2CH_3$ (4)
2) Deprotection of acid

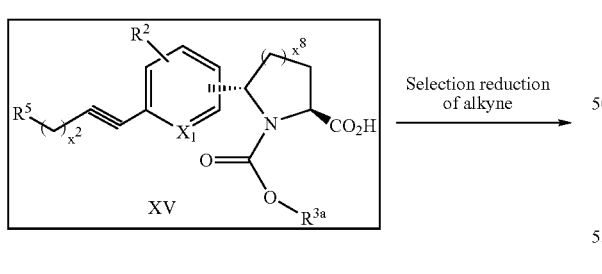

XV

Selection reduction of alkyne

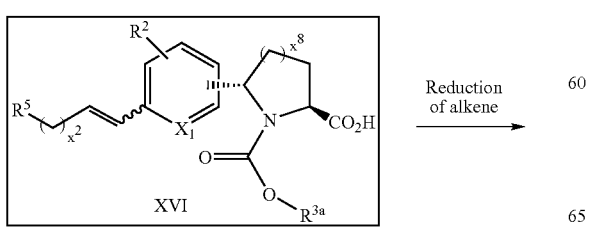

XVI

Reduction of alkene →

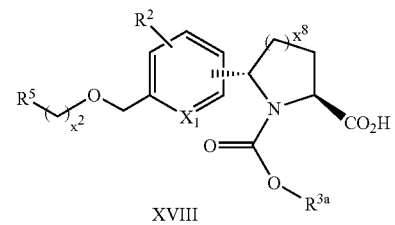

XVIII

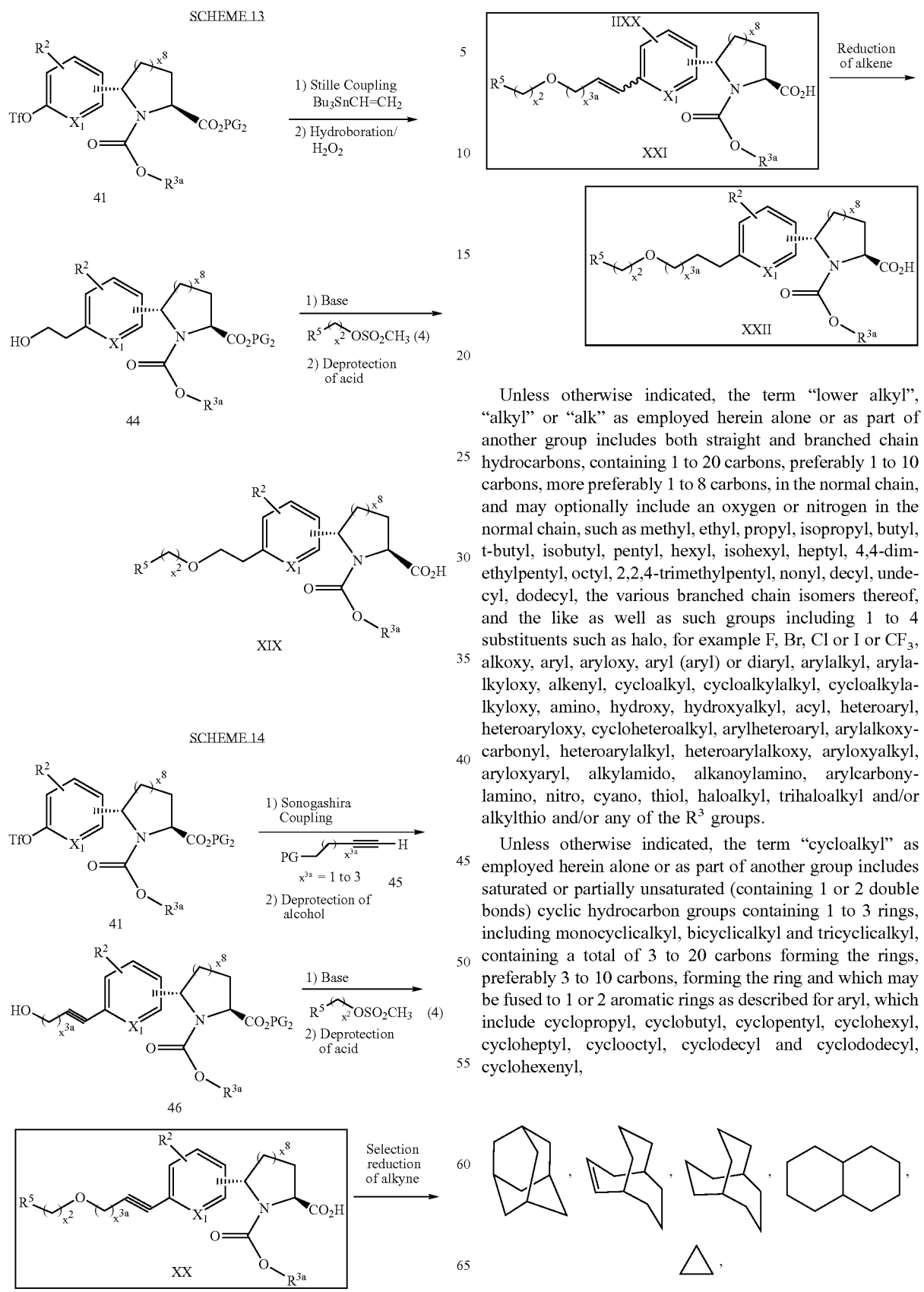

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl (aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

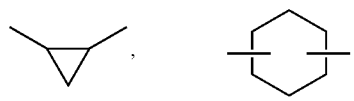

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH_2)_x^1$, $(CH_2)_x^2$, $(CH_2)_x^3$, $(CH_2)_x^4$, $(CH_2)_x^5$, $(CH_2)_x^6$, $(CH_2)_x^7$, $(CH_2)_x^8$, $(CH_2)_x^9$, $(CH_2)_m$, or $(CH_2)_n$ includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$, $(CH_2)_x^1$, $(CH_2)_x^2$, $(CH_2)_x^3$ or $(CH_2)_m$ or $(CH_2)_n$ group to form a cycloalkyl group therewith.

Examples of $(CH_2)_x$, $(CH_2)_x^1$, $(CH_2)_x^2$, $(CH_2)_x^3$, $(CH_2)_m$, $(CH_2)_n$, alkylene, alkenylene and alkynylene include

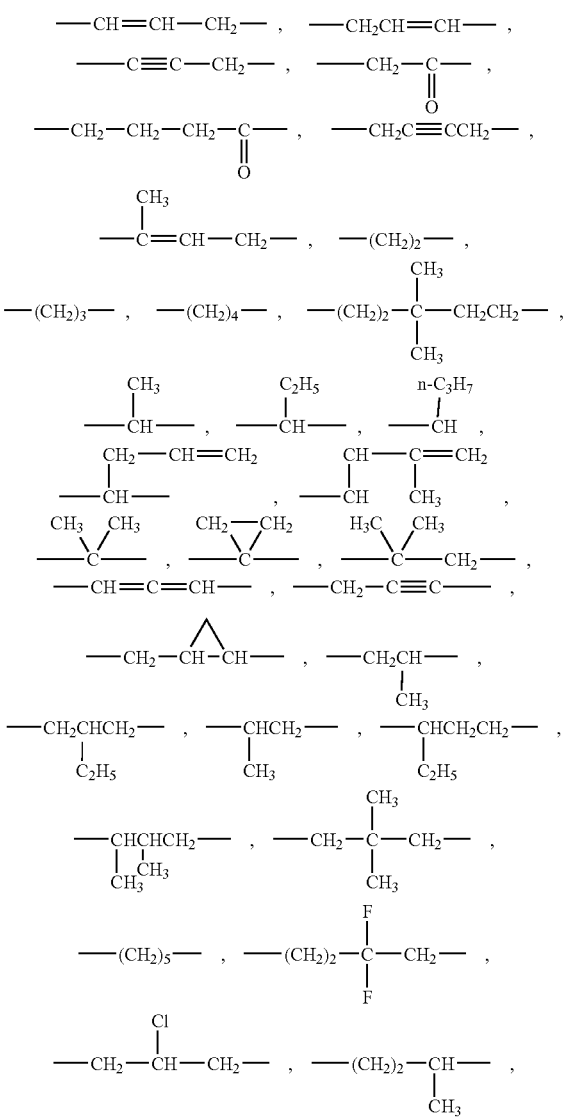

-continued

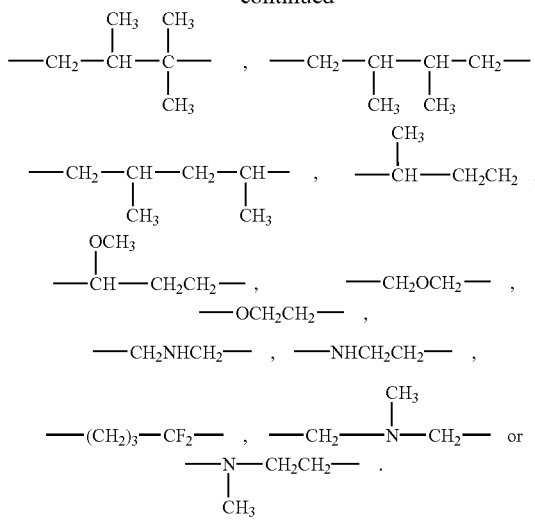

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

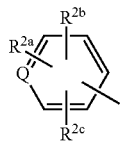

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

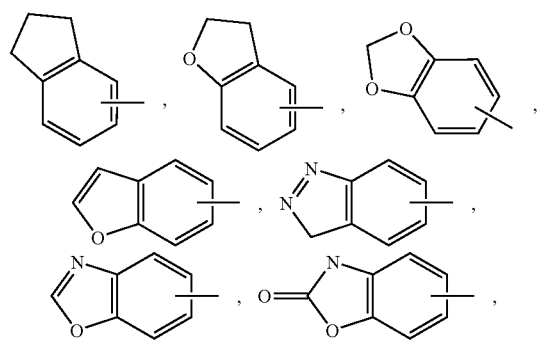

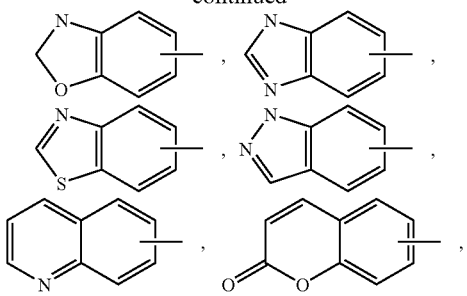

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

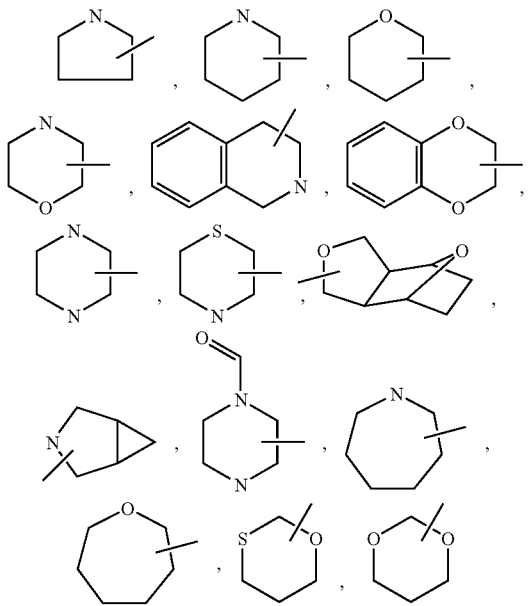

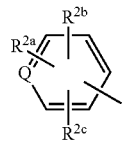

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

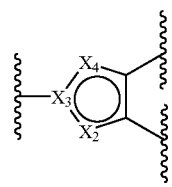

where Q is N, which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the substituents for alkyl or aryl set out above. Examples of heteroaryl groups include the following:

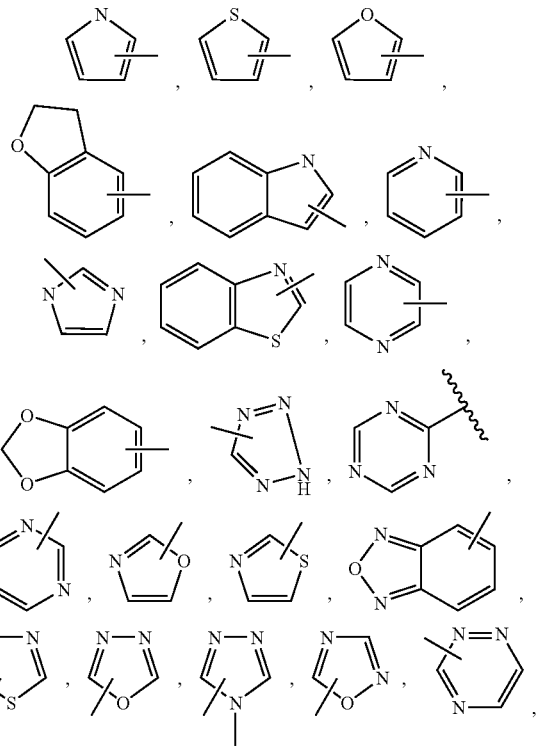

and the like.
Examples of

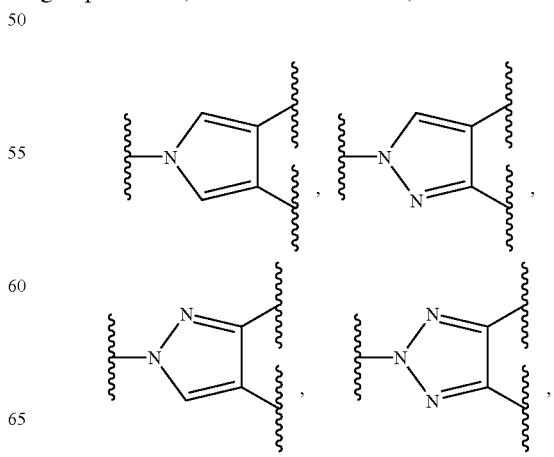

groups include, but are not limited to,

-continued

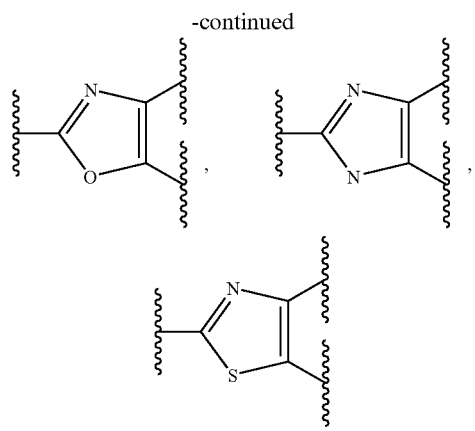

Examples of

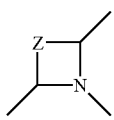

groups include, but are not limited to

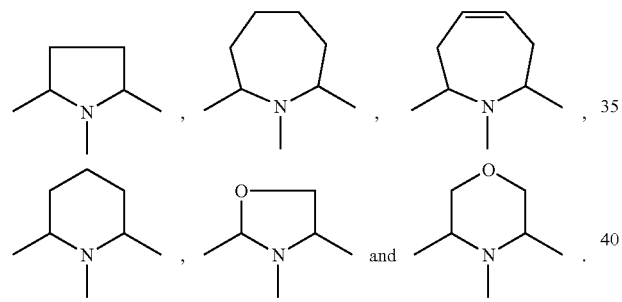

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups: (1-alkanoyloxy)alkyl such as,

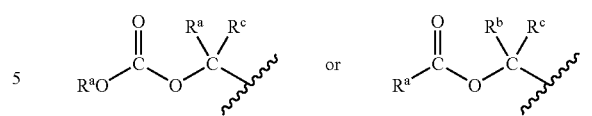

wherein $R^a$, $R^b$ and $R^c$ are H, alkyl, aryl or arylalkyl; however, $R^aO$ cannot be HO.

Examples of such prodrug esters $R^4$ include

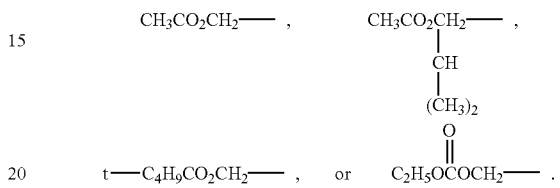

Other examples of suitable prodrug esters $R^4$ include

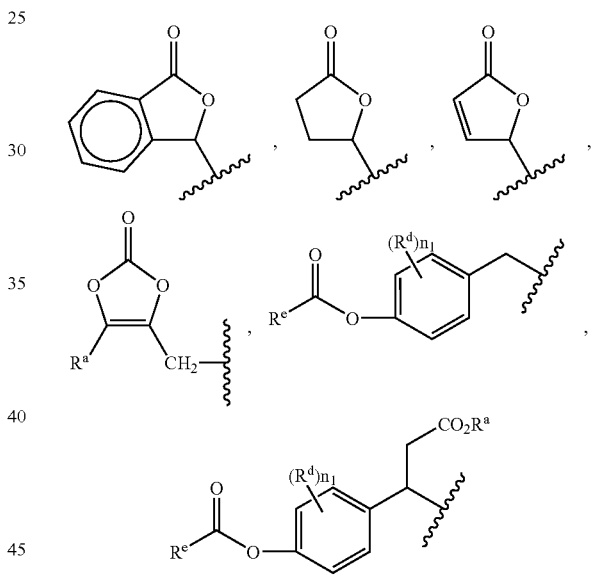

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents or lipid modulating agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

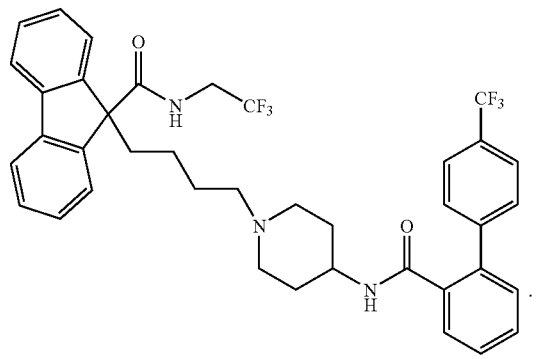

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's $SCH_{48461}$ as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. application Ser. No. 09/679,027, filed Oct. 4, 2000 (attorney file LA49 NP), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27 NP), employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(l-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79–022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]] 3R(*)]-2-[2-[[1-(ethoxy-carbonyl) -3-phenylpropyl]amino]-1-oxopropyl]-1,2,3,4-tetrahydro -6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®). Dosages employed will be as set out in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following Examples represent preferred embodiments of the invention.

The following abbreviations are employed in the Examples:

Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3$N=triethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
$LiAlH_4$=lithium aluminum hydride
n-BuLi=n-butyllithium
Pd/C=palladium on carbon
$PtO_2$=platinum oxide
KOH=potassium hydroxide
NaOH=sodium hydroxide
LiOH=lithium hydroxide
$K_2CO_3$=potassium carbonate
$NaHCO_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
$NaN(TMS)_2$=sodium hexamethyldisilazide or sodium bis(trimethylsilyl)amide
$Ph_3$P=triphenylphosphine
$Pd(OAc)_2$=Palladium acetate
$(Ph_3P)_4Pd°$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
$N_2$=nitrogen
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLE 1

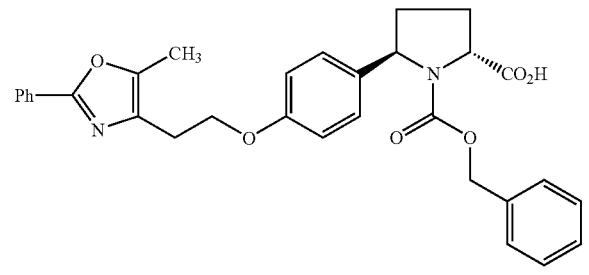

A

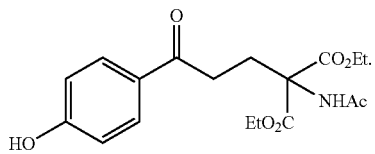

HCl gas was bubbled through absolute EtOH (3 mL) for 10 min, after which morpholine (1.92 g, 22 mmol) was added. Paraformaldehyde (0.66 g) and additional EtOH (1 mL) were successively added to the solid mixture. The reaction was stirred for 2 min, after which 4'-hydroxyacetophenone (2.0 g, 14.7 mmol) was added. The dark brown mixture was heated at 84° C. for 10 min, after which complete solution was achieved. The reaction was heated at reflux for 2 h, which resulted in extensive precipitation of solids. The mixture was cooled to RT, EtOH (3 mL) was added and the crude solid material was recovered by filtration, washed (CH$_2$Cl$_2$), and dried in vacuo to give Part A compound (2.77 g; 85%) as a beige solid.

B

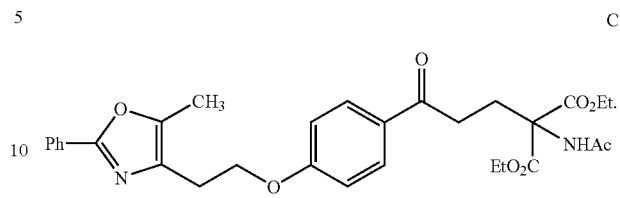

To a slurry of Part A compound (2.0 g, 7.4 mmol) in EtOH (3 mL) was added freshly prepared NaOEt solution (prepared from 0.5 g sodium and 4.5 mL EtOH; 7.4 mmol). The reaction mixture was stirred at RT for 0.5 h. Dimethyl sulfate (1.25 mL, 13.2 mmol) was then added. The reaction mixture was stirred at RT for 3 h, after which a mixture of diethylacetamidomalonate (1.6 g; 7.4 mmol) and freshly prepared NaOEt (prepared from 0.81 g sodium in 14 mL EtOH) was added. The reaction was stirred at RT for 1 h, then was heated at reflux for 2.5 h. The solution was cooled to RT, added cautiously into H$_2$O (10 mL) and acidified with concentrated HCl to pH ~2. The solution was extracted with EtOAc (3×). The combined organic extracts were washed with brine, dried (Na$_2$SO$_4$) and concentrated in vacuo. The oily residue was chromatographed (SiO$_2$; EtOAc:hexane 3:1) to give Part B compound (0.82 g, 29%) as an oil.

C

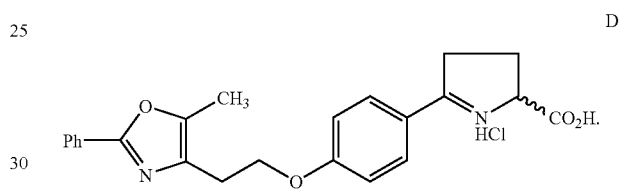

To a solution of Part B compound (0.74 g, 2.03 mmol) in THF (20 mL) at RT were successively added 2-(5-methyl-2-phenyloxazol-4-yl)ethanol (0.58 g, 2.85 mmol), Ph$_3$P (0.75 g, 3.05 mmol) and DEAD (0.478 mL, 1.5 eq). The reaction mixture was stirred at RT overnight, after which volatiles were removed in vacuo. The residue was chromatographed (SiO$_2$; hexanes:acetone 3:1) to give Part C compound (0.71 g, 63.4%) as a yellow oil.

D

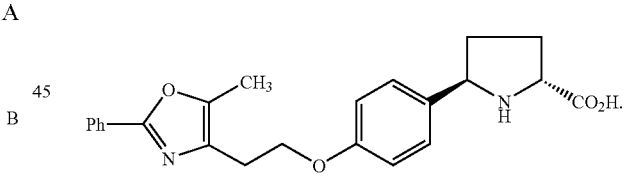

A mixture of Part C compound (0.71 g, 1.29 mmol) in aqueous 6N HCl (6 mL) was heated at reflux for 3 h. Volatiles were removed in vacuo to give a slightly pink solid residue, which was further dried overnight in vacuo to afford crude Part D compound as a foam, which was used without further purification in the next step.

E

To a mixture of Part D compound (603 mg, 1.4 mmol) in CH$_2$Cl$_2$ (25 mL) at RT was added NaBH(OAc)$_3$ (749 mg, 3.5 mmol). The reaction mixture was stirred at RT for 1 h (after which no starting material remained by analytical HPLC). Di-tert-butyl dicarbonate (1.08 g, 4.9 mmol) was then added to the reaction mixture, which was stirred at RT overnight. DMAP (50 mg; 0.41 mmol) was added and the reaction mixture was heated at 50° C. for 4 h. However, none of the desired Boc-protected amino acid was obtained, and only unprotected amino acid was recovered. The mixture was concentrated in vacuo and divided into three portions for SCX cartridge purification (United Technology CUBCX12M6 cartridges, with 2 g sorbent). The SCX cartridge was successively conditioned with CH$_2$Cl$_2$, washed with CH$_2$Cl$_2$ (20 mL), MeOH (10 mL) and finally 2M ammonia in MeOH (15 mL). The combined NH$_3$/MeOH eluents were concentrated in vacuo to give Part E compound (150 mg; 27% yield) as a white solid.

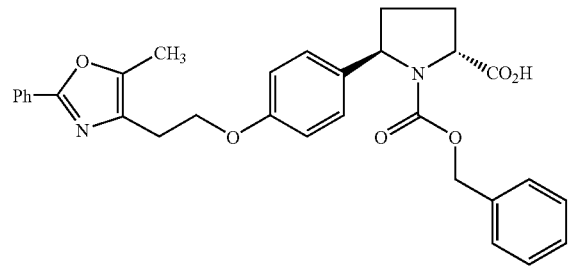

A mixture of Part E compound (0.030 g, 0.076 mmol) in THF (1 mL) and aqueous Na$_2$CO$_3$ (8 mg in 0.9 mL H$_2$O, 2.2 mmol) was stirred at RT for 10 min, after which benzyl chloroformate (13.1 μL, 0.092 mmol) was added. After 0.5 and 1 h, more benzyl chloroformate (0.8 and 1.2 equivalents respectively) was added. The reaction mixture was sonicated for several minutes and then heated briefly (heat gun). After another 0.5 h, the reaction mixture was neutralized with 1N HCl and extracted with EtOAc (2×). The combined organic extracts were concentrated in vacuo. The residue was purified by preparative HPLC (YMC S5 ODS 30×250 mm reverse phase column; flow rate=25 mL/min; 30 min continuous gradient from 70:30 A:B to 100% B, where solvent A=90:10:0.1 H$_2$O:MeOH:TFA and solvent B =90:10:0.1 MeOH:H$_2$O:TFA) to give the racemic title compound (15 mg; 38%) as a white solid. [M+H]+=527.4

EXAMPLE 2

A

B

To a solution of Example 1 Part D compound (362 mg, 0.85 mmol) in EtOH (10 mL) at RT was added NaBH$_4$ (32 mg, 0.85 mmol). The reaction mixture was stirred at RT for 4 h. The mixture was concentrated in vacuo and divided into three portions for SCX cartridge purification (United Technology CUBCX12M6 cartridges, with 2 g sorbent). The SCX cartridge was conditioned with CH$_2$Cl$_2$, after which the compound was eluted with CH$_2$Cl$_2$ (20 mL), MeOH (10 mL) and finally 2M ammonia in MeOH (15 mL). The combined NH$_3$/MeOH eluents were concentrated in vacuo to give the intermediate pyrrolidine-acid as a slightly yellow oil (278 mg). A solution of this material in saturated methanolic HCl (10 ml) was stirred at RT overnight after which volatiles were removed in vacuo. The residue was load onto a SCX cartridge for purification (United Technology CUBCX12M6 cartridges, with 2 g sorbent). The SCX cartridge was successively conditioned with CH$_2$Cl$_2$, after which the compound was eluted with CH$_2$Cl$_2$ (20 mL), MeOH (10 mL) and finally 2M ammonia in MeOH (15 mL). The combined NH$_3$/MeOH eluents were concentrated in vacuo to give Part A compound (300 mg, 90%) as a foam.

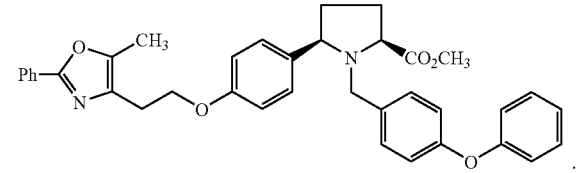

To a mixture of Part A compound (265 mg, 0.65 mmol), 4-phenoxybenzaldehyde (323 mg, 1.63 mmol) and NaBH(OAc)$_3$ (415 mg, 1.96 mmol) in DCE (8 mL) was added glacial acetic acid (12 drops). The reaction mixture was stirred at RT overnight, after which volatiles were removed in vacuo. The residue was diluted with H$_2$O (5 mL) and thoroughly extracted with EtOAc (40 mL). The organic phase was dried (MgSO$_4$) and concentrated in vacuo. The residue was loaded onto two SCX cartridge (3 g). The cartridges were successively washed with CH$_2$Cl$_2$ (30 mL) and CH$_2$Cl$_2$:MeOH (3:1; 20 mL). The product was then eluted with excess 1M NH$_3$ in MeOH. This final fraction was concentrated in vacuo and the mixture was chromatographed (SiO$_2$; stepwise gradient from 100:1 to 50:1 CH$_2$Cl$_2$:EtOAc) to give Part B compound (145 mg, 38%) as well as Part C compound (the trans isomer; 55 mg, 14%).

Part C Compound

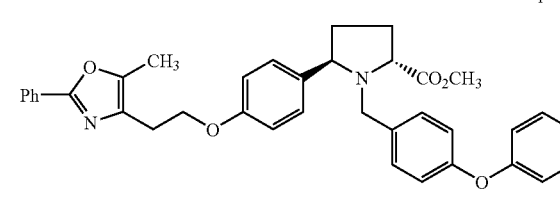

D

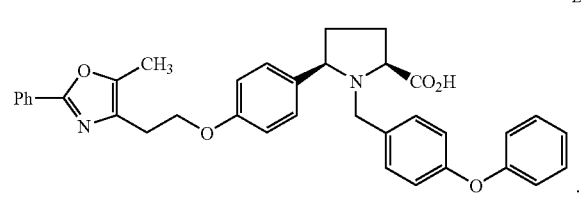

A solution of Part B compound (85 mg, 0.145 mmol) and LiOH (12.1 mg, 0.288 mmol) in THF:H$_2$O (2 mL of a 1:1 solution) was stirred at RT overnight. Volatiles were removed in vacuo and H$_2$O (2 mL) was added. The pH of the solution was adjusted to 5 with aqueous 1N HCl. This was thoroughly extracted with EtOAc (2×30 mL). The combined organic extracts were dried (MgSO$_4$) and concentrated in vacuo. The residue was loaded onto two SCX cartridge (2 g). The cartridges were successively washed with CH$_2$Cl$_2$ (30 mL) and CH$_2$Cl$_2$:MeOH (3:1; 20 mL). The product was then obtained by elution with excess 1M NH$_3$ in MeOH. This final fraction was concentrated in vacuo to give the racemic title compound (72 mg, 87%) as an oil. [M+H]+=575.3

EXAMPLE 3

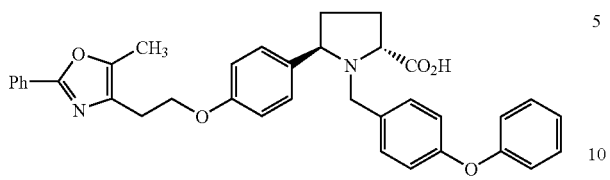

A solution of Example 2 Part C compound (32 mg, 0.054 mmol) and LiOH (4.6 mg, 0.143 mmol) in THF:H$_2$O (2 mL of a 1:1 solution) was stirred at RT overnight. More LiOH (4.6 mg, 0.143 mmol) and MeOH (0.5 mL) were added to the mixture, which was stirred at RT for another 24 h. The pH of the solution was adjusted to 5 with aqueous 1N HCl. Volatiles were removed in vacuo; the residue was dissolved in CH$_2$Cl$_2$ (0.5 mL) and loaded onto a SCX cartridge (2 g). The cartridge was successively washed with CH$_2$Cl$_2$ (30 mL) and MeOH (20 mL). The product was then eluted with excess 1M NH$_3$ in MeOH. This final fraction was concentrated in vacuo to give the racemic title compound (26 mg, 83%) as an oil. [M+H]+=575.3

EXAMPLE 4

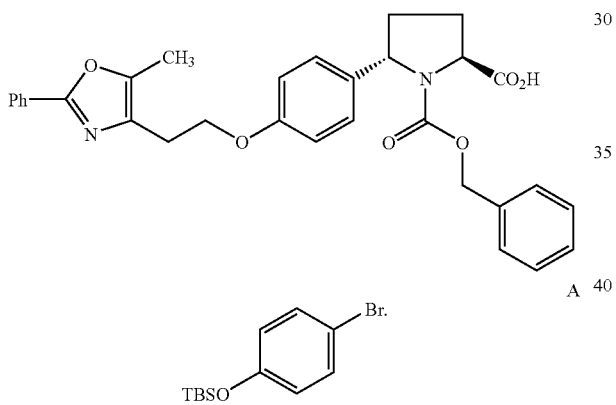

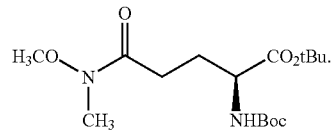

A

To a 0° C. solution of 4-bromophenol (10.0 g; 57.8 mmol) in CH$_2$Cl$_2$ were successively added TBSCl (9.14 g; 60.6 mmol), Et$_3$N (12.6 mL; 90.4 mmol) and DMAP (400 mg; 3.27 mmol). The reaction mixture was stirred at RT for 3 h; the resulting solids were filtered off and the filtrate was concentrated in vacuo. The residue was chromatographed (SiO$_2$; hexane) to give Part A compound (13.26 g; 80%) as a clear colorless oil.

B

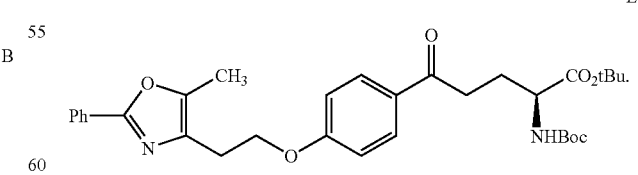

To a mixture of Boc-L-Glutamic acid t-butyl ester (3.03 g; 9.98 mmol), HOBT (1.79 g; 13.2 mmol), NMM (3.29 mL; 29.9 mmol) and N-methoxy N-methylamine hydrochloride (1.07 g; 11.0 mmol) in CHCl$_3$ (45 mL) was added EDCI.HCl (2.31 g; 12.0 mmol). The mixture was stirred at RT overnight for 12 h. Volatiles were removed in vacuo and the residue was partitioned between H$_2$O (150 mL) and EtOAc (250 mL). The aqueous phase was extracted with EtOAc (250 mL); the combined organic extracts were dried (MgSO$_4$) and concentrated in vacuo. The residue was chromatographed (SiO$_2$; stepwise gradient from 3:1 to 1:1 hexane:EtOAc) to give Part B compound (3.36 g; 97%) as a colorless oil.

C

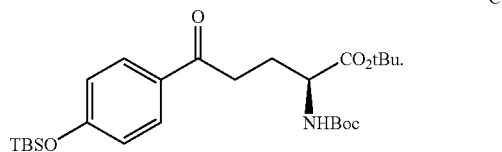

To a solution of Part A compound (4.86 g; 17.0 mmol) in THF (80 mL) at −78° C. under Ar was added n-BuLi (6.79 mL of a 2.5M solution in hexanes; 17.0 mmol) dropwise. The mixture was stirred at −78° C. for 0.5 h and was then added dropwise by cannula to a solution of Part B compound (2.18 g; 6.3 mmol) in THF (30 mL) at −20° C. over 45 min. The mixture was stirred at −20° C. overnight, then quenched with saturated aqueous NH$_4$Cl (100 mL). The aqueous layer was extracted with EtOAc (2×200 mL). The combined organic extracts were dried (MgSO$_4$), concentrated in vacuo and chromatographed (SiO$_2$; stepwise gradient from hexane to 5:1 hexane:EtOAc) to give Part C compound (1.52 g; 51%) as a yellow oil.

D

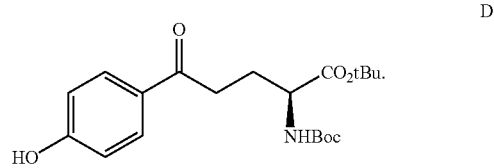

To a solution of Part C compound (0.784 g; 1.59 mmol) in THF (30 mL) was added TBAF (1.9 mL of a 1 M solution in THF) followed by HOAC (109 μL). The reaction mixture was stirred at RT for 40 min, at which point TLC showed that starting material had been consumed. Volatiles were removed in vacuo, and the residue was dissolved in a mixture of EtOAc and hexane. Precipitated solids were filtered off, and the filtrate was concentrated in vacuo. The residue was chromatographed (SiO$_2$; stepwise gradient from 3:1 hexane:EtOAc to 100% EtOAc) to give Part D compound (396 mg; 66%) as a yellow solid.

E

To a solution of Part D compound (396 mg; 1.04 mmol) in THF (6 mL) was added the 2-phenyl-5-methyl-oxazole-4-ethanol (360 mg; 0.77 mmol), followed by Ph$_3$P (0.463 g; 1.88 mmol) and DEAD (0.296 mL; 1.88 mmol). The reaction mixture was stirred at RT overnight. Volatiles were removed in vacuo and the residue was chromatographed (SiO$_2$; stepwise gradient from 3:1 to 1:1 hexane:EtOAc) to give Part E compound (500 mg; 86%) as a viscous oil.

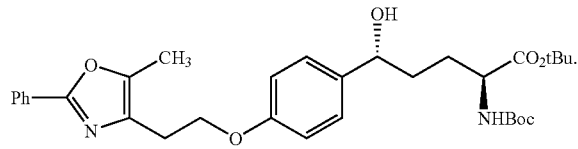

F

A mixture of (S)-2-methyl oxazaborolidine (0.551 mL of a 1M solution in toluene) and BH$_3$.THF (1.53 mL of a 1M solution in THF) was stirred at RT for 5 min under Ar and then cooled to −20° C. A solution of Part E compound (500 mg; 0.886 mmol) in THF (3 mL) was added at −20° C. for 45 min. The reaction mixture was then quenched with MeOH (1 mL) at 0° C., stirred for another 15 min, then more MeOH (3 mL) was added Volatiles were removed in vacuo and the residue was chromatographed (SiO$_2$; stepwise gradient from 2:1 to 1:1 hexane:EtOAc). Methanol was added to the residue and the solution was stirred for 30 min before volatiles were removed in vacuo to give Part F compound (470 mg; 94%) as an oil.

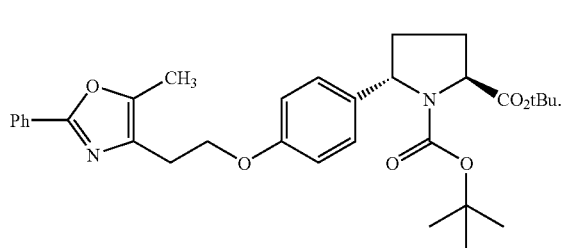

G

To a 0° C. solution of Part F compound (470 mg; 0.83 mmol) in THF (12 mL) were successively added methanesulfonyl chloride (96 µL; 1.24 mmol) and Et$_3$N (0.227 mL; 1.62 mmol). The reaction mixture was allowed to warm to RT and stirred at RT overnight. Volatiles were removed in vacuo and the residue was chromatographed (SiO$_2$; stepwise gradient from 4:1 to 2:1 hexane:EtOAc) to give the desired pyrrolidine Part G compound (impure) as well as recovered starting material (287 mg; 0.509 mmol). A 0° C. solution of the recovered Part F compound in THF (5 mL) was treated as above with methanesulfonyl chloride (59 µL; 0.76 mmol) and Et$_3$N (0.130 mL; 0.93 mmol) for 2 h. Volatiles were removed in vacuo and the residue was combined with the impure Part G compound and chromatographed (SiO$_2$; stepwise gradient from 4:1 to 2:1 hexane:EtOAc) to give pure Part G compound (334 mg; 73%) as a viscous oil.

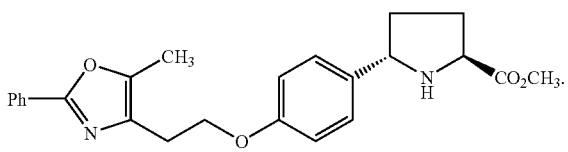

H

A saturated HCl/MeOH solution was made by bubbling HCl gas into MeOH (5 mL) for 3 min and this was then added to Part G compound (320 mg; 0.584 mmol). This solution was stirred at RT overnight, then volatiles were removed in vacuo. The residue was dissolved in EtOAc (100 mL) and H$_2$O (5 mL). Saturated aqueous NaHCO$_3$ was added to the solution until the pH was 8. The aqueous phase was extracted (EtOAc; 30 mL). The combined organic extracts were dried (MgSO4) and concentrated in vacuo to give a residual oil. This was chromatographed (SiO$_2$; stepwise gradient from 1:1 hexane:EtOAc to EtOAc) to give Part H compound (175 mg; 74%) as an oil.

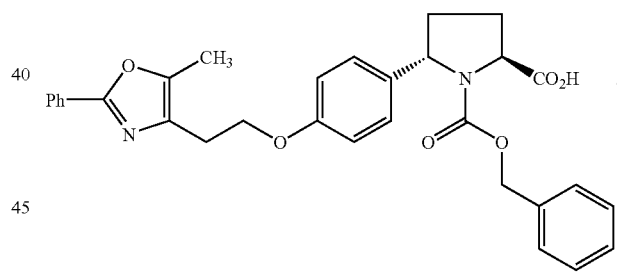

I

To a solution of Part H compound (50 mg; 0.125 mmol) in CH$_2$Cl$_2$ (1 mL) at RT were successively added benzyl chloroformate (19 µL; 0.132 mmol) and Et$_3$N (34 µL; mmol). After 5 min, DMAP (2 mg) was added, and the reaction mixture was stirred at RT for 1 h, after which more benzyl chloroformate, Et$_3$N and DMAP (same quantities as above) were added. The reaction was stirred at RT for 48 h. The reaction was still incomplete at this point. Volatiles were removed in vacuo to give a residual oil; pyridine (0.6 mL) and benzyl chloroformate (38 µL; 0.27 mmol) were added and the reaction was stirred for 30 min at RT and at 60° C. for 30 min. The reaction appeared to be complete at this point. Volatiles were removed in vacuo, and the residue was chromatographed (SiO$_2$; stepwise gradient from 4:1 to 1:1 hexane:EtOAc). A second chromatography (CHSil 12MC cartridge; 4:1 to 1:1 hexane:EtOAc) provided Part I compound (45 mg; 67%) as an oil.

J

A solution of Part I compound (40 mg; 0.074 mmol) in MeOH:THF (1 mL of a 3:7 solution) and aqueous LIOH (3 mg [0.071 mmol] in 0.7 mL) was stirred at RT for 2h. Additional aqueous LiOH (0.5 equiv) was added and the mixture was stirred at RT for 20h. Volatiles were removed in vacuo; H$_2$O (2 mL) was added and the pH of the solution was adjusted to 6 with aqueous 1M HCl. EtOAc (60 mL) was added and the mixture was stirred at RT for 1 h until all the precipitated solids were dissolved. The organic layer was washed with water (5 mL), dried (MgSO$_4$) and concentrated in vacuo. The residue was chromatographed twice, first using a CUSil 12M6 cartridge (stepwise gradient from 1:1 hexane:EtOAc to EtOAc) and then on SiO$_2$ (stepwise gradient from CHCl$_3$ to 5:1 CHCl$_3$:MeOH) to provide, after lyophiization from dioxane, the pure title compound (S, S isomer; 32 mg; 82%) as a white solid. Chiral HPLC (Chiracel OJ-R column, isocratic 60:40 B:A; where A=H$_2$O+0.1% trifluoroacetic acid, B=CH$_3$CN+0.1% trifluoroacetic acid; retention time=10.63 min at a flow rate of 1.5 mL/min). The retention time of the $2^{nd}$ enantiomer (R, R) is 13.98 min. [M+H]+=527.4 $\alpha_D$ (c=5.0 mg in 1 mL MeOH) =−0.23°

EXAMPLE 5

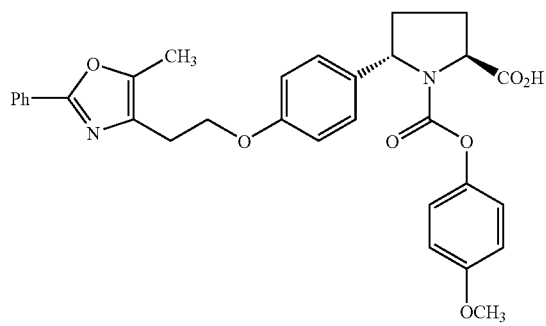

A

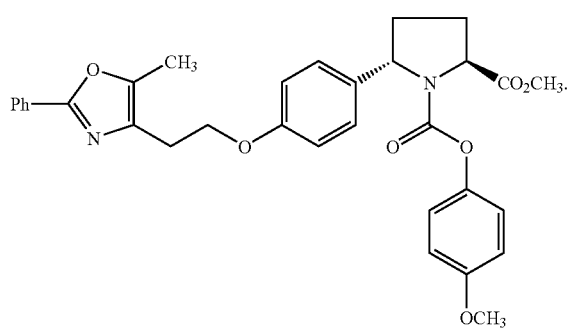

B

To a solution of the Example 4 Part H compound (39 mg; 0.096 mmol) pyridine (1 mL) at RT were successively added 4-methoxy phenyl chloroformate (24 μL; 0.16 mmol) and DMAP (6 mg; 0.049 mmol). Additional pyridine (1 mL) was added after the initial precipitate was formed. The yellow reaction mixture was stirred at RT for 5 h, after which volatiles were removed in vacuo. The residue was chromatographed (SiO$_2$; stepwise gradient from 4:1 to 2:1 hexane:EtOAc) to give Part A compound (50 mg; 94%) as a foam.

A solution of Part A compound (36 mg; 0.065 mmol) and LiOH (4 mg; 0.095 mmol) in THF:H$_2$O (2 mL of a 1:1 solution) was stirred at RT overnight. Volatiles were removed in vacuo and H$_2$O (3 mL) was added. The pH of the solution was adjusted to 5 with aqueous 1M HCl. This was extracted with EtOAc (30 mL); the organic layer was concentrated in vacuo and chromatographed ((SiO$_2$; stepwise gradient from CHCl$_3$ to 5:1 CHCl$_3$:MeOH) to give, after lyophilization from dioxane, the title compound (28 mg; 80%) as a white powder. [M+H]+=543.3 $\alpha_D$ (c=5.1 mg in 1 mL MeOH)=−0.495°

EXAMPLE 6

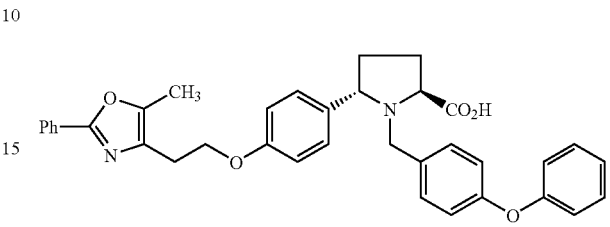

The title compound was prepared using the 2-step sequence (reductive amination and hydrolysis of the methyl ester) as described for Example 9 (see below) from Example 4 Part H compound. [M+H]+=575.3

EXAMPLE 7

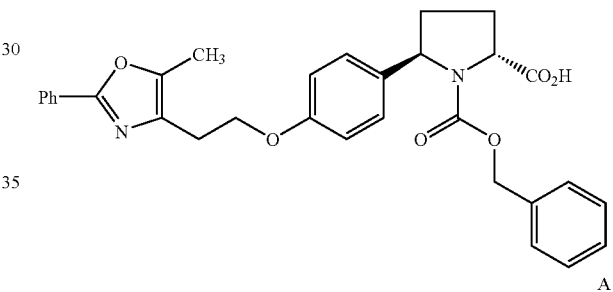

A

Part A compound was prepared from Boc-D-Glutamic acid t-butyl ester and N-methoxy N-methylamine hydrochloride in CHCl$_3$ using EDCI.HCl/HOBT as described for Example 4 Part B compound.

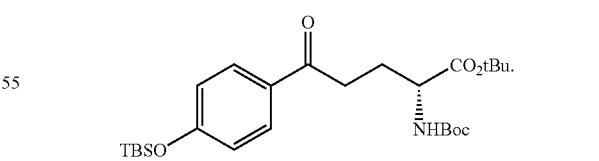

B

To a solution of Example 4 Part A compound (4.86 g; 17.0 mmol) in THF (80 mL) at −78° C. under Ar was added n-BuLi (6.79 mL of a 2.5M solution in hexanes; 17.0 mmol) dropwise. The mixture was stirred at −78° C. for 0.5 h and was then added dropwise by cannula to a solution of Part A compound (2.18 g; 6.3 mmol) in THF (30 mL) at −20° C. over 45 min. The mixture was stirred at −20° C. overnight, then quenched with saturated aqueous NH$_4$Cl (10 mL). The aqueous layer was extracted with EtOAc (2×150 mL). The combined organic extracts were dried (MgSO$_4$), concentrated in vacuo and chromatographed (SiO$_2$; stepwise gradient from hexane to 5:1 hexane:EtOAc) to give Part B compound (1.22 g; 39%) as a yellow oil.

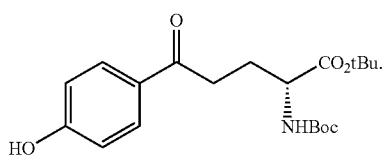

C

To a solution of Part B compound (1.21 g; 2.45 mmol) in THF (46 mL) were successively added TBAF (3.04 mL of a 1 M solution in THF; 3.04 mmol) and HOAC (168 μL). The reaction mixture was stirred at RT for 2 h, at which point TLC showed that starting material had been consumed. Volatiles were removed in vacuo, and the residue was dissolved in EtOAc. Precipitated solids were filtered off, and the filtrate was concentrated in vacuo. The residue was chromatographed (SiO$_2$; stepwise gradient from 3:1 hexane:EtOAc to 100% EtOAc) to give Part C compound (560 mg; 60%) as a yellow solid.

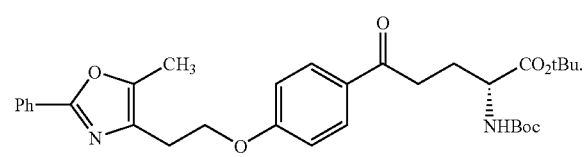

D

To a solution of the phenol (548 mg; 1.45 mmol) in THF (8 mL) was added 2-phenyl-5-methyl-oxazole-4-ethanol (509 mg; 2.51 mmol), followed by Ph$_3$P (639 mg; 2.43 mmol) and DEAD (408 μL; 2.59 mmol). The reaction mixture was stirred at RT for 5 h. Volatiles were removed in vacuo and the residue was chromatographed (SiO$_2$; stepwise gradient from 3:1 to 2:1 hexane:EtOAc) to give Part D compound (522 mg; 64%) as a viscous oil.

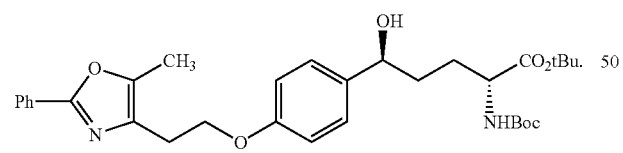

E

A mixture of (R)-2-methyl oxazaborolidine (551 μL of a 1M solution in toluene) and BH$_3$.THF (1.53 mL of a 1M solution in THF) was stirred at RT for 5 min under Ar and then cooled to −20° C. A solution of Part D compound (500 mg; 0.89 mmol) in THF (3 mL) was added dropwise at −20° C. The reaction was stirred at −20° C. for 15 min & maintained at −20° C. for 2 h. The mixture was then cautiously quenched with MeOH (4 mL) at −20° C., then stirred for 1 h. Volatiles were removed in vacuo, additional MeOH (4 mL) was added and the mixture stirred at RT for 2 h. Volatiles were removed and the residue was chromatographed (SiO$_2$; stepwise gradient from 2:1 to 1:1 hexane:EtOAc). Methanol was added to the residue and the solution was stirred for 30 min before volatiles were removed in vacuo to give Part E compound (500 mg; 100%) as a white foam.

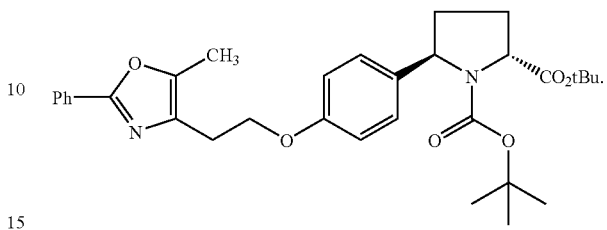

F

To a 0° C. solution of Part E compound (500 mg; 0.89 mmol) in THF (12 mL) were successively added methanesulfonyl chloride (150 μL; 1.94 mmol) and Et$_3$N (360 μL; 2.29 mmol). The reaction mixture was allowed to warm to RT and stirred at RT for 4 h. Volatiles were removed in vacuo and the residue was chromatographed (SiO$_2$; stepwise gradient from 4:1 to 2:1 hexane:EtOAc) to give Part F compound (430 mg; 88%) as a colorless viscous oil.

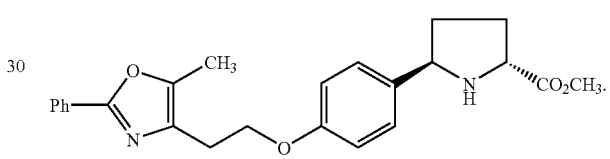

G

A saturated HCl/MeOH solution was made by bubbling HCl gas into MeOH (5 mL) for 5 min and this solution was then added to Part F compound (400 mg; 0.73 mmol). This solution was stirred at RT overnight, after which volatiles were removed in vacuo. The residue was dissolved in EtOAc (150 mL) and H$_2$O (3 mL). Saturated aqueous NaHCO$_3$ was added to the solution until the pH was 8. The aqueous phase was extracted (EtOAc; 50 mL). The combined organic extracts were dried (MgSO$_4$) and concentrated in vacuo. The residue was chromatographed (SiO$_2$; stepwise gradient from 1:1 hexane:EtOAc to EtOAc) to provide Part G compound (205 mg; 69%) as an oil.

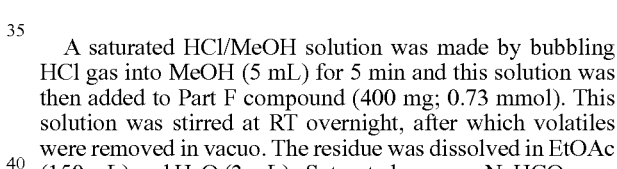

H

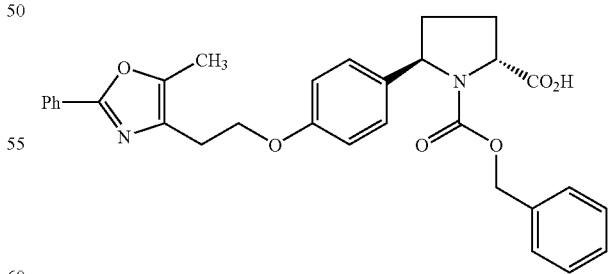

To a solution of Part G compound (25 mg; 0.046 mmol) in pyridine (1 mL) at RT were successively added benzyl chloroformate (17 μL; 0.12 mmol) and DMAP (4 mg). The yellow reaction mixture was stirred at RT overnight. The reaction was incomplete at this point. Volatiles were removed in vacuo. The residue was chromatographed (SiO$_2$;

stepwise gradient from 3:1 to 1:1 hexane:EtOAc) to give Part H compound (20 mg; 85%) as an oil.

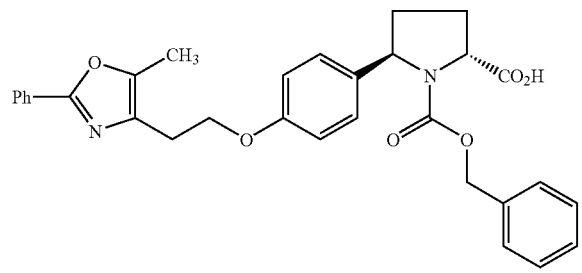

I

A solution of Part H compound (20 mg; 0.037 mmol) in MeOH:THF (0.55 mL of a 3:7 solution) and aqueous LiOH (3 mg [0.071 mmol] in 0.4 mL H$_2$O) was stirred at RT. Volatiles were then removed in vacuo; H$_2$O (1 mL) was added and the pH of the solution was adjusted to 5 with aqueous 1M HCl. The mixture was thoroughly extracted with EtOAc (25 mL). The organic phase was dried (Na$_2$SO$_4$) and concentrated in vacuo. The residue was chromatographed (SiO$_2$; stepwise gradient from CHCl$_3$ to 5:1 CHCl$_3$:MeOH) to provide, after lyophiization from dioxane, the title compound (13 mg; 67%) as a white powder. Chiral HPLC (Chiracel OJ-R column, isocratic 60:40 B:A; where A=H$_2$O+0.1% trifluoroacetic acid, B=CH$_3$CN+0.1% trifluoroacetic acid; retention time=13.98 min at a flow rate of 1.5 mL/min). [M+H]+=527.4 $\alpha_D$ (c=5.0 mg in 1 mL MeOH)=+0.265°

EXAMPLE 8

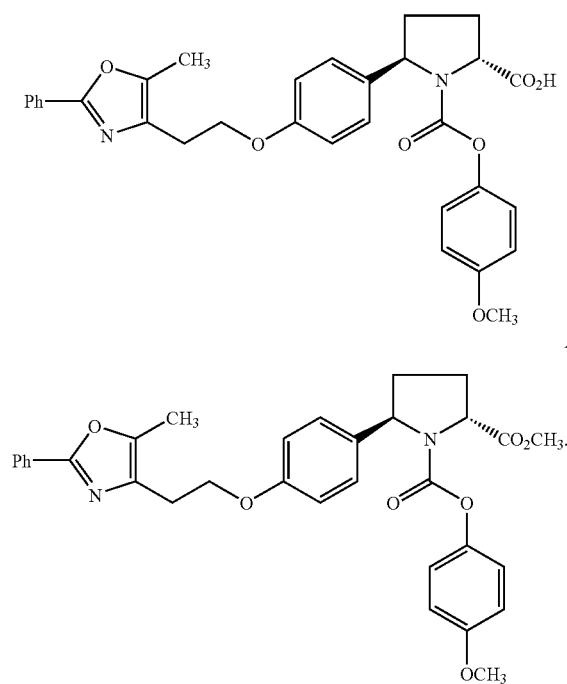

A

To a solution of Example 7 Part G compound (25 mg; 0.062 mmol) pyridine (1 mL) at RT were successively added 4-methoxy phenyl chloroformate (23 μL; 0.16 mmol) and DMAP (4 mg). The yellow reaction mixture was stirred at RT overnight, after which volatiles were removed in vacuo. The residue was chromatographed (SiO$_2$; stepwise gradient from 3:1 to 2:1 hexane:EtOAc) to give Part A compound (22 mg; 63%) as a colorless oil.

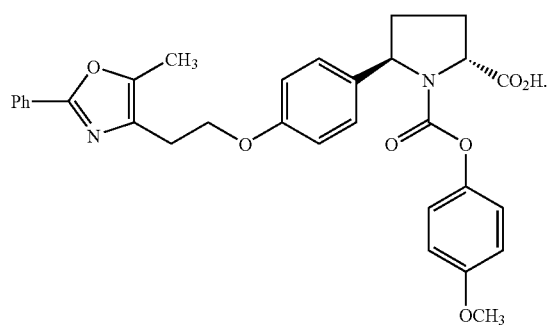

B

A solution of Part A compound (22 mg; 0.039 mmol) and LIOH (3 mg; 0.07 mmol) in THF:H$_2$O (1 mL of a 1:1 solution) was stirred at RT overnight. Volatiles were removed in vacuo and H$_2$O (1 mL) was added. The pH of the solution was adjusted to 5 with aqueous 1M HCl. This was thoroughly extracted with EtOAc (25 mL). The organic phase was concentrated in vacuo and chromatographed (SiO$_2$; stepwise gradient from CHCl$_3$ to 5:1 CHCl$_3$:MeOH) to give, after lyophilization from dioxane, the title compound (the R, R isomer, 19 mg; 89%) as a white powder. [M+H]+=543.3 $\alpha_D$ (c=5.1 mg in 1 mL MeOH)=+0.45°

EXAMPLE 9

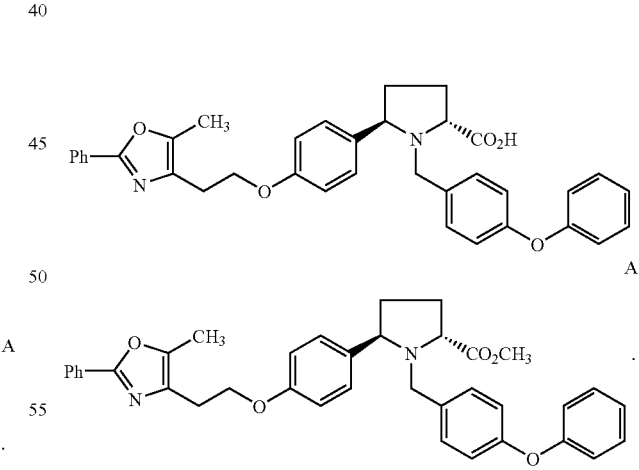

A

To a solution of Example 7 Part G compound (30 mg; 0.074 mmol) and 4-phenoxybenzaldehyde (38 mg; 0.19 mmol) in DCE (1 mL) was added HOAc (2 drops). The reaction mixture was stirred at RT for 3 h, after which NaBH(OAc)$_3$ (45 mg; 0.21 mmol) was added in one portion. Stirring was continued at RT for 2 h, after which volatiles were removed in vacuo. The residue was chromatographed twice (SiO$_2$; 4:1 hexane:EtOAc followed by hexane:

CH$_2$Cl$_2$:EtOAc 5:5:0.5) to give Part A compound (28 mg; 64%) as a colorless oil.

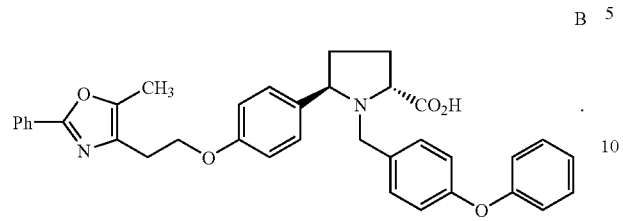
B

A solution of Part A compound (28 mg; 0.048 mmol) and aqueous LiOH (8 mg; 0.18 mmol in 0.5 mL H$_2$O) in THF:MeOH (1.5 mL of a 2:1 solution) was stirred at RT overnight. Volatiles were removed in vacuo and H$_2$O (2 mL) was added. The pH of the solution was adjusted to 5 with aqueous 1M HCl. This was thoroughly extracted with EtOAc (30 mL). The organic phase was concentrated in vacuo and chromatographed (SiO$_2$O; stepwise gradient from CHCl$_3$ to 5:1 CHCl$_3$:MeOH) to give, after lyophilization from dioxane, the title compound (24 mg; 88%) as a white powder. [M+H]+=575.3 α$_D$ (c=5.0 mg in 1 mL CH$_2$Cl$_2$)=+0.287°

EXAMPLES 10 to 12

Analogs (Examples 10–12) were prepared according to the synthetic sequence described above for Example 4, except that 3-bromo-phenol was used as the starting material instead of 4-bromo-phenol.

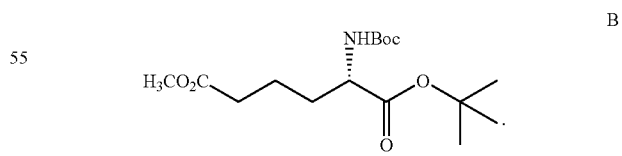

(S, S Series)

| Example No. | R | [M + H]+ |
|---|---|---|
| 10 | ![structure] | 543.3 |
| 11 | ![structure] | 527.4 |
| 12 | ![structure] | 575.3 |

EXAMPLE 13

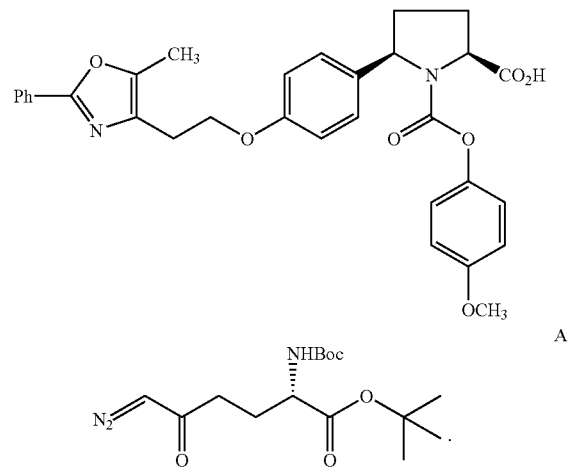
A

A solution of diazomethane in Et$_2$O was prepared according to the following procedure. To a 0° C. mixture of 40% KOH (12.5 mL) and Et$_2$O (50 mL) was added 1-methyl-3-nitro-1-nitrosoguanidine) portionwise (4.42 g; 30 mmol). The yellow mixture was swirled several times during each addition (after gas evolution had ceased). After 10 min, the ethereal diazomethane layer was decanted. The aqueous layer was washed with Et$_2$O (25 mL). The combined diazomethane-containing organic extracts were dried (KOH) at 0° C.

To a −20° C. solution of methyl N-Boc-L-glutamate (3.03 g, 10.0 mmol) in THF (50 mL) were successively added isobutyl chloroformate (1.94 mL, 15.0 mmol) and N-methyl morpholine (1.64 mL, 15.0 mmol). The mixture was stirred at −20° C. for 1 h. The white precipitate was filtered and washed with dry THF (20 mL). The combined filtrates containing the mixed anhydride was cooled to −5° C. and added cautiously to the above solution of diazomethane in Et$_2$O at 0° C. and stirred for 4 h at RT. HPLC analysis indicated that the reaction was complete. N$_2$ was bubbled through the mixture for 20 min. The reaction mixture was partitioned between H$_2$O (50 mL) and Et$_2$O (250 mL). The organic phase was dried (MgSO$_4$), then concentrated in vacuo to provide Part A compound (1.8 g; 55%) as an oil, which was used in the next reaction without further purification.

B

![structure B]

To a solution of Part A compound (1.8 g; 5.5 mmol) in MeOH (7.2 mL) was added a solution of silver benzoate (0.18 g; 0.79 mmol) in Et$_3$N (3.6 mL). The reaction mixture became dark, which was concomitant with N$_2$ evolution. The reaction mixture was stirred at RT for min, then filtered through a pad of Celite®. The filtrate was concentrated in vacuo; the residue was chromatographed (SiO$_2$; hex:

EtOAc=2:1) to give Part B compound as a colorless oil (1.55 g; 85%).

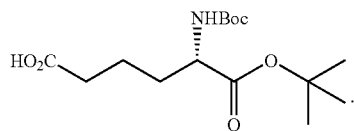

To a solution of Part B compound (1.53 g; 4.62 mmol) in THF (10 mL) was added an aqueous LiOH solution (0.213 g in 8 mL H$_2$O). The mixture was stirred at RT for 2 h. The reaction was acidified to pH=4–5 with 1M aq HCl. The organic phase was removed and the mixture was extracted with EtOAc (2×50 mL). The combined organic extracts were dried (MgSO$_4$) and concentrated in vacuo to give Part C compound (1.42 g; 97%) as a colorless solid.

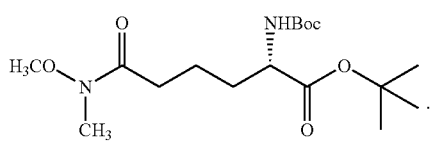

To a solution of Part C compound (1.42 g; 4.48 mmol), HOBT (0.87 g; 6.27 mmol), MeONHMe.HCl (0.539 g; 5.53 mmol) and N-methyl morpholine (1.52 mL; 14.4 mmol) in CHCl$_3$ (18 mL) was added EDCI.HCl (1.15 g; 6.0 mmol). The reaction mixture was stirred at RT for 6 h, after which it was partitioned between water (30 mL) and CH$_2$Cl$_2$ (100 mL). The organic phase was dried (MgSO$_4$) and concentrated in vacuo; the residue was chromatographed (SiO$_2$; stepwise gradient from 3:1 to 1:1 hex:EtOAc) to give Part D compound (1.33 g; 83%) as a white solid.

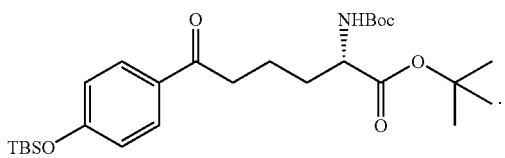

To a −78° C. solution of 4-t-butyldimethylsiloxy bromobenzene (1.78 g; 6.22 mmol) in THF (30 mL) under AR was added dropwise a solution of n-BuLi in hexane (2.5 mL of a 2.5M solution; 6.25 mmol) and the reaction was stirred at −78° C. for 30 min. This aryllithium solution was cannulated over 15 min into a −20° C. solution of BMS-379685 Part D compound (750 mg; 2.08 mmol) in THF (9 mL). The reaction was allowed to warm to RT and stirred at RT for 5 h, then quenched with saturated aqueous NH$_4$Cl. The solution was then partitioned between H$_2$O (20 mL) and EtOAc (100 mL). The organic phase was dried (MgSO$_4$) and concentrated in vacuo. The residue was chromatographed (SiO$_2$; stepwise gradient from 10:1 to 5:1 hex:EtOAc) to give Part E compound (668 mg; 68%) as an oil.

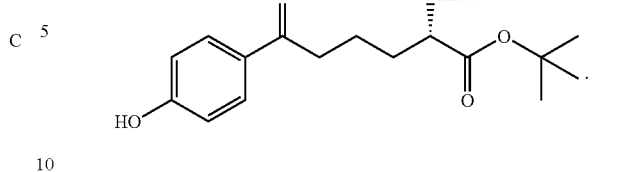

To a solution of Part E compound (668 mg; 1.32 mmol) in THF (26 mL) were added TBAF (1.44 mL of a 1M solution in THF) and acetic acid (82 µL; 1.44 mmol). The reaction was stirred at RT for 1 h. Volatiles were moved in vacuo. The residue was chromatographed (SiO$_2$; stepwise gradient from 3:1 hex:EtOAc to 100% EtOAc) to give Part F compound (435 mg; 84%) as an oil.

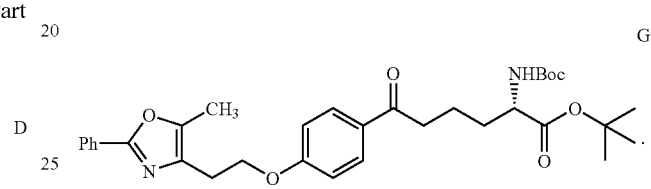

To a solution of Part F compound (600 mg; 1.53 mmol) in DMF (10 mL) was added 2-phenyl 5-methyl oxazole-4-ethanol mesylate (649 mg; 2.31 mmol) followed by powdered K$_2$CO$_3$ (527 mg; 3.81 mmol) . The reaction mixture was stirred at 80° C. for 4 h. Analytical HPLC indicated that all starting material had been consumed at this point. The reaction mixture was partitioned between Et$_2$O (200 mL) and H$_2$O (50 mL) . The organic phase was washed with water (2×50 mL), dried (MgSO4) and concentrated in vacuo. The residue was chromatographed (SiO$_2$; stepwise gradient from 5:1 to 2:1 hex:EtOAc) to give Part G compound (520 mg; 59%) as an oil.

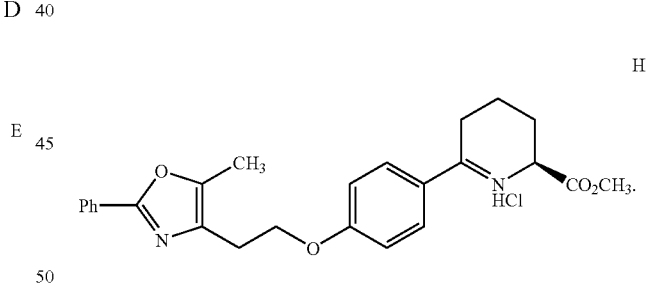

A solution of Part G compound (85 mg; 0.148 mmol) in a saturated HCl/MeOH solution (3 mL) was stirred at RT for 36 h. Volatiles were removed in vacuo to give Part H compound (79 mg crude material) as a foam which was used in the next step without further purification.

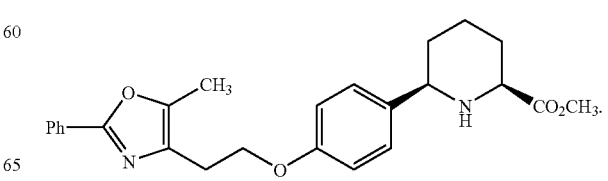

To a solution of Part H compound (79 mg) in DCE (2 mL) at RT was added NaBH(OAc)₃ (79 mg; 0.373 mmol). The reaction was stirred at RT for 20 h. Volatiles were removed in vacuo and the residue was loaded onto an SCX cartridge (2 g). The cartridge was successively washed with CH₂Cl₂ (30 mL), CH₂Cl₂:MeOH (10:1; 20 mL) and MeOH (20 mL). The product was then eluted with excess 1M NH₃ solution in MeOH. This final fraction was concentrated in vacuo to give Part I compound (55 mg; 88% over 2 steps) as an oil.

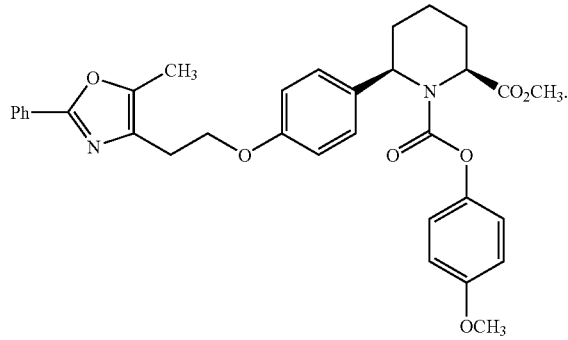

J

To a solution of Part I compound (28 mg; 0.067 mmol) in pyridine (0.8 mL) were added 4-methoxyphenyl chloroformate (31 mg; 0.167 mmol) and DMAP (6 mg; mmol). The reaction was stirred at RT for 30 min, then heated at 80° C. for 1 min, then at RT for another 1 h. Volatiles were removed in vacuo. The residue was chromatographed (SiO₂; stepwise gradient from 4:1 to 2:1 hex:EtOAc) to give Part J compound (32 mg; 84%) as a viscous oil.

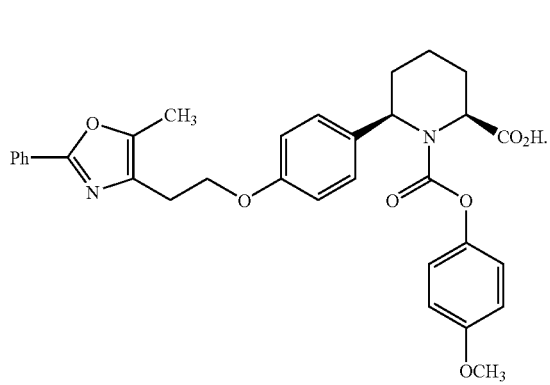

K

To a solution of Part J compound (23 mg; 0.040 mmol) in THF (0.5 mL) and MeOH (0.15 mL) was added a solution of aqueous LiOH (9 mg in 0.5 mL H₂O). The reaction was stirred at RT overnight for 12 h, then acidified to pH 4 by addition of 1M aqueous HCl. Volatiles were removed in vacuo and the residue partitioned between water (10 mL) and EtOAc (18 mL). The organic phase was dried (MgSO₄) and concentrated in vacuo. The residue was chromatographed (SiO₂; stepwise gradient from 1:1 hex:EtOAc to 100% EtOAc). Final purification using preparative HPLC (YMC ODS reverse phase column; continuous gradient from 60%A:40%B to 100% B over 30 min, where solvent A=90:10:0.1 H₂O:MeOH:TFA and solvent B=90:10:0.1 MeOH:H₂O:TFA; flow rate=25 mL/min) to give the title compound (13 mg; 58%) as a viscous oil. [M+H]+=557.2

EXAMPLE 14

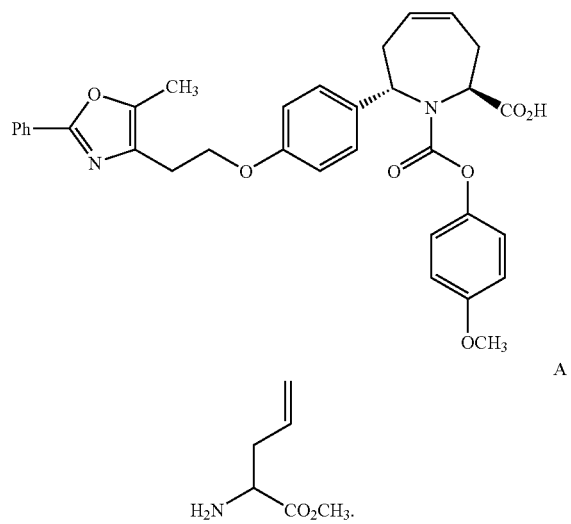

HCl gas was bubbled through a mixture of (±) allyl glycine (5.00 g; 43.4 mmol) in MeOH (25 mL) for 5 min. The reaction mixture was stirred at RT for 48 h, after which volatiles were removed in vacuo. The residue was dissolved in EtOAc (250 mL) and washed with saturated aq. NaHCO₃. The organic phase was dried (MgSO₄) and concentrated in vacuo to give Part A compound (3.92 g; 70%) as a colorless oil.

B

A mixture of the aldehyde (609 mg; 1.98 mmol)

Part A compound (281 mg; 2.18 mmol) and 4A molecular sieves (100 mg) in CH₂Cl₂ (5 mL) was stirred at RT for 40 h, after which the reaction to form the intermediate imine was complete by ¹H NMR.

To a mixture of indium metal (452 mg; 3.93 mmol) in DMF (4 mL) was added allyl bromide (513 μL; 5.92 mmol). The mixture was stirred at RT for 30 min. The solution of the intermediate imine from above was then added and the reaction was stirred at RT for 24 h. The reaction mixture was partitioned between Et₂O (100 mL) and water. The organic phase was dried (MgSO4) and concentrated in vacuo. The residue was chromatographed (SiO$_2$; stepwise gradient from 3:1 to 1:1 hex:EtOAc) to give Part B compound (684 mg; 75%) as an oil.

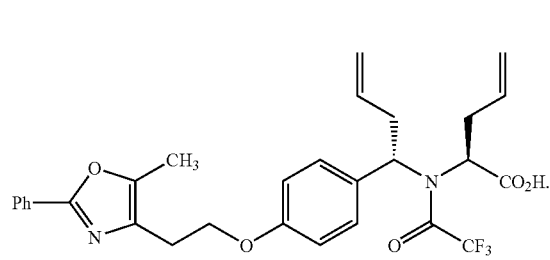

C

To a solution of Part B compound (93 mg; 0.20 mmol) in CH$_2$Cl$_2$ (0.7 mL) were successively added Et$_3$N (85 µL; 0.60 mmol) and TFAA (57 µL; 0.404 mmol). The slightly yellow reaction mixture was stirred at RT for 24 h. Volatiles were removed in vacuo and the residue was chromatographed (SiO$_2$; hex:EtOAc 4:1) to give Part C compound (104 mg; 93%) as a viscous oil.

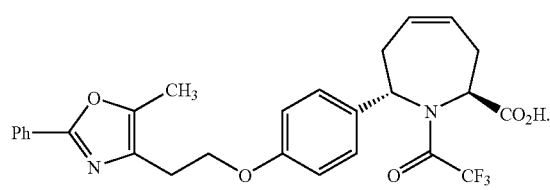

D

A solution of Part C compound (600 mg; 1.08 mmol) in CH$_2$Cl$_2$ (15 mL) was degassed by bubbling a stream of argon through it for 10 min. The Grubbs olefin metathesis catalyst (54 mg; 0.066 mmol) was then added under argon. The reaction was stirred at RT for 16 h. Volatiles were removed in vacuo and the residue was chromatographed (SiO$_2$; stepwise gradient from 4:1 to 2:1 hex:EtOAc) to give Part D compound (460 mg; 81%) as an oil.

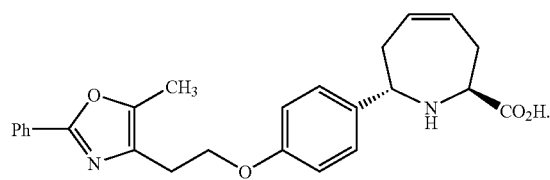

E

A solution of Part D compound (90 mg; 0.17 mmol) in a saturated K$_2$CO$_3$/MeOH solution (3 mL) was stirred at RT overnight at RT. Water (3 mL) and additional K$_2$CO$_3$ (45 mg; 0.325 mmol) were then added and the mixture heated at 50° C. for 24 h, after which the methyl ester had been hydrolyzed. KOH (45 mg; 0.80 mmol) was added and the mixture was stirred at RT overnight; more KOH (100 mg; 1.78 mmol) was added and the mixture was heated at 55° C. for 48 h, after which the trifluoroamide had been hydrolyzed. Volatiles were removed in vacuo and the residue was acidified with 1M aqueous HCl solution (to pH=7). The aqueous phase was extracted with EtOAc (2×25 mL); the combined organic extracts were dried (MgSO$_4$) and concentrated in vacuo to provide Part E compound (70 mg; 98%) as a foam.

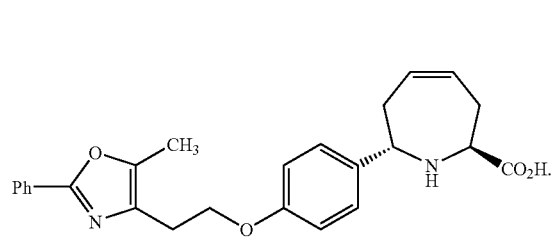

F

A mixture of Part E compound (35 mg; 0.084 mmol) in a saturated solution of HCl in MeOH (1.5 mL) was stirred overnight. Volatiles were removed in vacuo and the residue was basified with saturated aqueous NaHCO$_3$. The aqueous phase was extracted with EtOAc (30 mL). The organic phase was concentrated in vacuo and the residue was chromatographed (SiO$_2$; stepwise gradient from 3:2 to 1:1 hex:EtOAc) to give Part F compound (24 mg; 67%) as an oil.

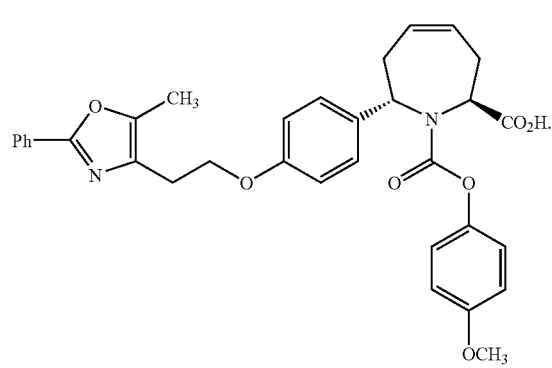

G

To a solution of Part F compound (10 mg; 0.023 mmol) in pyridine (0.5 mL) were successively added DMAP (2 mg; 0.016 mmol) and 4-methoxyphenyl chloroformate (10.8 mg; 0.058 mmol) and the reaction mixture was stirred at RT for 3 h. Volatiles were removed in vacuo and the residue was chromatographed (SiO$_2$; stepwise gradient from 2:1 to 1:5 hex:EtOAc) to give Part G compound (10.5 mg; 78%) as an oil.

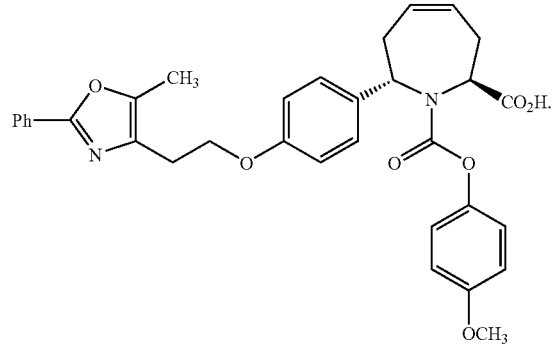

H

A mixture of Part G compound (5 mg; 0.0086 mmol) in a saturated solution of K$_2$CO$_3$ in MeOH (0.5 mL) was stirred at RT for 1 h, then heated at 60° C. for 3 h. Another batch of Part G compound (25 mg; 0.043 mmol) in saturated K$_2$CO$_3$ in MeOH (2.5 mL) was heated at 60° C. for 3 h. The two reactions were combined and voatiles were removed in vacuo. The residue was dissolved in water (1 mL) and the pH was acidified to 6 with 1M aqueous HCl. The aqueous phase was extracted with EtOAc (20 mL). The organic phase was concentrated in vacuo and the residue was purified by preparative HPLC (YMC S5 ODS reverse phase column; 30×250 mm; flow rate=25 mL/min; 30 min continuous gradient from 70:30 A:B to 100% B, where solvent A=90:10:0.1 H$_2$O:MeOH:TFA and solvent B=90:10:0.1 MeOH:H$_2$O:TFA) to give the title compound (9 mg; 31%) as a white foam. [M+H]+=569.3

EXAMPLE 15

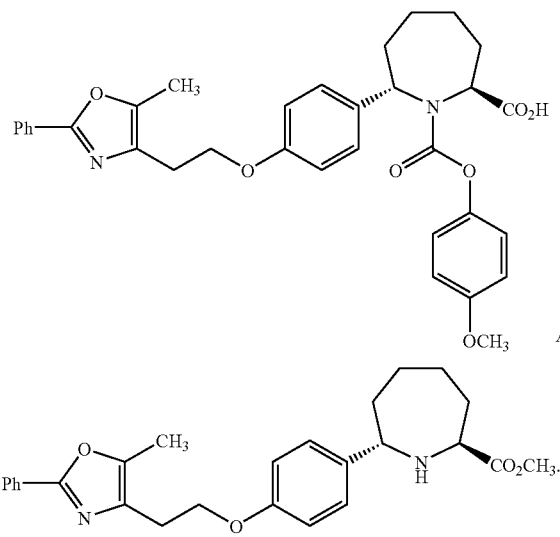

A

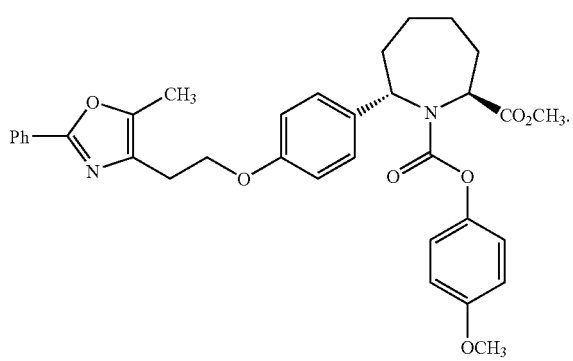

A mixture of Example 14 Part F compound (77 mg; 0.18 mmol) and 10% Pd/C (20 mg) in MeOH (10 mL) was stirred under an atmosphere of hydrogen for 1 h at RT. The catalyst was then filtered off (Celite®) and the filtrate was concentrated in vacuo to give Part A compound (70 mg; 91%) as an oil.

B

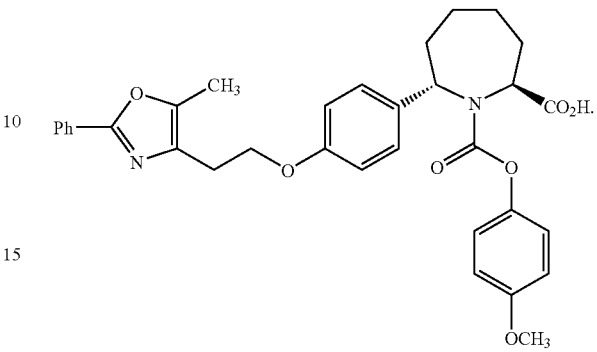

To a solution of Part A compound (30 mg; 0.069 mmol) in pyridine/DMF (700 μL/100 μL) was added DMAP (5 mg) and 4-methoxyphenyl chloroformate (26 μL; 0.17 mmol). The reaction mixture was heated at 60° C. for 5 min and stirred at RT for 1 h. Volatiles were removed in vacuo and the residue was chromatographed (SiO$_2$; stepwise gradient from 2:1 to 1:1 hex:EtOAc) to give Part B compound (32 mg; 79%) as an oil.

C

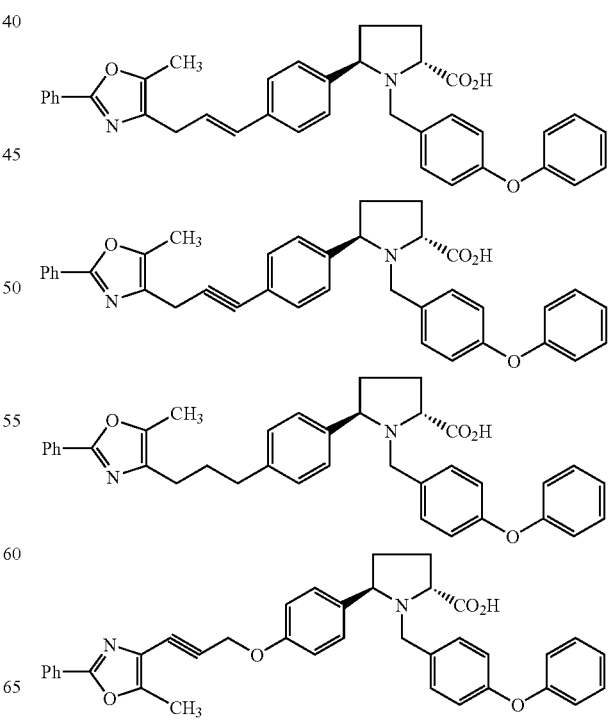

To a solution of Part B compound (32 mg; 0.055 mmol) in MeOH (4 mL) was added K$_2$CO$_3$ (25 mg; 0.18 mmol) in H$_2$O (10 drops). The reaction mixture was heated at 60° C. for 15 h. At this point LC/MS indicated that the reaction was incomplete. More K$_2$CO$_3$ (15 mg) in H$_2$O (4 drops) was added and the reaction was heated at 60° C. for another 5 h. Volatiles were removed in vacuo and the residue was acidified with excess 1 M aqueous HCl until the pH was <7. The mixture was extracted with EtOAc (2×) and the combined organic extracts were concentrated in vacuo. The residue was purified by preparative HPLC ((YMC S5 ODS reverse phase column; 30×250 mm; flow rate=25 mL/min; 30 min continuous gradient from 75:25 A:B to 100% B, where solvent A=90:10:0.1 H$_2$O:MeOH:TFA and solvent B=90:10:0.1 MeOH:H$_2$O:TFA) to give the title compound (12 mg; 38%) as a white foam. [M+H]$^+$=571.3

Following the procedures set out in the above Examples and in the reaction schemes, the following exemplary compounds may be prepared:

-continued

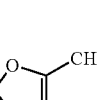

What is claimed is:
1. A compound which has the structure

wherein $X_m$ is a bond, $C_{1-2}$ alkylene, $C_2$ alkenylene, allenyl or $C_2$ alkynylene;
$X_n$ is a bond, $C_{1-2}$ alkylene, $C_2$ alkenylene, allenyl or $C_2$ alkynylene;
Q is C or N;
A is $C_{1-5}$ alkylene, $C_{2-5}$ alkenylene, allenyl or $C_{2-5}$ alkynylene; or A is $(CH_2)_{x^1}$, where $x^1$ is 2 to 5, with an alkenyl bond or an alkynyl bond embedded in the chain; or A is $X_x^2$—O—$X_x^3$ where $X_x^2$ is a bond, $C_{1-5}$ alkylene, $C_{2-5}$ alkenylene, allenyl or $C_{2-5}$ alkynylene and $X_x^3$ is a bond, $C_{1-5}$ alkylene, $C_{2-5}$ alkenylene, allenyl or $C_{2-5}$ alkynylene, provided that at least one of $X_x^2$ and $X^{x3}$ is other than a bond;
$X^1$ is CH or N;
$X^2$ is C, N, O or S;
$X^3$ is C or N;
$X^4$ is C, N, O or S, provided that at least one of $X^2$, $X^3$ and $X^4$ is N;
in each of $X^1$ through $X^4$, as defined above, C may include CH;
$R^1$ is H or alkyl;
$R^2$ is H, alkyl, alkoxy, halogen, amino or substituted amino;
$R^{2a}$, $R^{2b}$ and $R^{2c}$ may be the same or different and are selected from H, alkyl, alkoxy, halogen, amino or substituted amino;
$R^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cyclo heteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkylcarbonyl, aryloxyalkylo xycarbonyl, arylalkylsulfonyl, aryithiocarbonyl, arylalkenylsulfonyl, heteroarylsulfonyl, arylsulfonyl, alkoxyarylalkyl, heteroarylalkoxycarbonyl, aryiheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonyiheteroarylalkyl, heteroarylarylalkyl, arylcarbonyllieteroarylalkyl, heteroaryloxyarylalkyl, arylalkenylheteroarylalkyl, arylaminoarylalkyl, aminocarbonylarylarylalkyl;
Y is $CO_2R^4$ (where $R^4$ is H or alkyl, or a prodrug ester) or Y is a C-linked 1-tetrazole, a phosphinic acid of the structure $P(O)(OR^{4a})R^5$ (where $R^{4a}$ is H or a prodrug ester which is a methyl, ethyl or benzyl ester, $R^5$ is alkyl or aryl) or a phosphonic acid of the structure $P(O)(OR^{4a})_2$;
Z is $(CH_2)_{x^4}$ where $x^4$ is 2;
including all stereoisomers thereof, and a pharmaceutically acceptable salt thereof, wherein the term prodrug ester refers to carboxylic acid esters, phosphorus acid esters, and esters where $R^4$ is

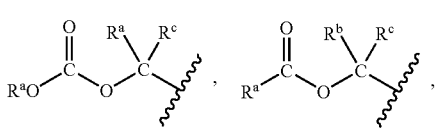

wherein $R^a$, $R^b$ and $R^c$ are H, alkyl, aryl or arylalkyl;

provided that $R^aO$ cannot be HO,
or $R^4$ is

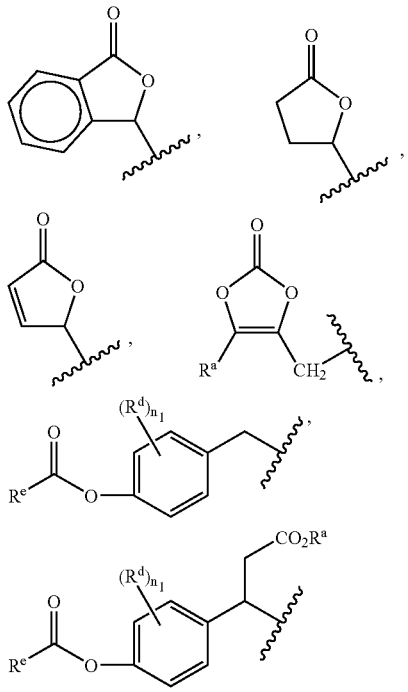

wherein $R^a$ is H, alkyl, arylalkyl or aryl; $R^d$ is H, alkyl, halogen or alkoxy, $R^e$ is alkyl, aryl, arylalkyl or alkoxyl, and $n_1$ is 0, 1 or 2.

2. The compound as defined in claim 1 wherein $X_m$ is $(CH_2)_m$ where m is 0, 1 or 2, $X_n$ is $(CH_2)_n$ where n is 0, 1 or 2.

3. The compound as defined in claim 1 wherein $X_1$ is CH.

4. The compound as defined in claim 1 wherein $R^{2a}$, $R^{2b}$ and $R^{2c}$ are each H, Z is —$CH_2$—$CH_2$—, A is —$CH_2CH_2$—.

5. The compound as defined in claim 1 wherein $R^1$ is lower alkyl, $X_2$ is O, $X_3$ is C, and $X_4$ is N.

6. The compound as defined in claim 1 wherein A is —$X_x^2$—O—$X_x^3$—.

7. The compound as defined in claim 1 wherein $X_n$ is a bond and $X_m$ is a bond or $CH_2$.

8. The compound as defined in claim 1 wherein $R^3$ is arylalkyl, aryloxycarbonyl or arylalkyloxycarbonyl.

9. The compound as defined in claim 8 wherein $R^3$ is alkoxyaryloxycarbonyl or phenoxyarylalkyl.

10. A compound having the structure

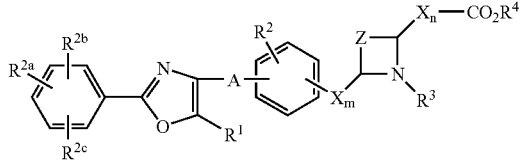

wherein $X_m$ is a bond, $C_{1-2}$ alkylene, $C_2$ alkenylene, allenyl or $C_2$ alkynylene;
$X_n$ is a bond, $C_{1-2}$ alkylene, $C_2$ alkenylene, allenyl or $C_2$ alkynylene;
A is $C_{1-5}$ alkylene, $C_{2-5}$ alkenylene, allenyl or $C_{2-5}$ alkynylene; or A is $(CH_2)_x^1$, where $x^1$ is 2 to 5, with an alkenyl bond or an alkynyl bond embedded in the chain; or A is $X_x^2$—O—$X_x^3$ where $X_x^2$ is a bond, $C_{1-5}$ alkylene, $C_{2-5}$ alkenylene, allenyl or $C_{2-5}$ alkynylene and $X_x^3$ is a bond, $C_{1-5}$ alkylene, $C_{2-5}$ alkenylene, allenyl or $C_{2-5}$ alkynylene, provided that at least one of $X_x^2$ and $X_x^3$ is other than a bond, $R^1$ is H or alkyl;

$R^2$ is H, alkyl, alkoxy, halogen, amino or substituted amino;

$R^{2a}$, $R^{2b}$ and $R^{2c}$ may be the same or different and are selected from H, alkyl, alkoxy, halogen, ammo or substituted amino;

$R^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, aryiheteroarylalkyl, arylalkylarylalkyl, aryloxyarylalkyl, haloalkoxyarylo xycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkylcarbonyl, aryloxyalkyloxycarbonyl, arylalkylsulfonyl, aryithiocarbonyl, arylalkenylsulfonyl, heteroarylsulfonyl, arylsulfonyl, alkoxyarylalkyl, heteroarylalkoxycarbonyl, aryiheteroarylalkyl, alkoxyarylcarbonyl, aryloxyheteroarylalkyl, heteroarylalkylo xyarylalkyl, arylarylalkyl, arylalkenylarylalkyl, arylalkoxyarylalkyl, arylcarbonylarylalkyl, alkylaryloxyarylalkyl, arylalkoxycarbonyiheteroarylalkyl, heteroarylarylalkyl, arylcarbonyiheteroarylalkyl, heteroaryloxyarylalkyl, arylalkenylheteroarylalkyl, arylaminoarylalkyl, or aminocarbonylarylarylalkyl;

$R^4$ is H or alkyl, or a prodrug ester;

Z is $(CH_2)_x^4$ where $x^4$ is 2;

including all stereoisomers thereof, and a pharmaceutically acceptable salt thereof, wherein the term prodrug ester refers to carboxylic acid esters, phosphorus acid esters, and esters where $R^4$ is

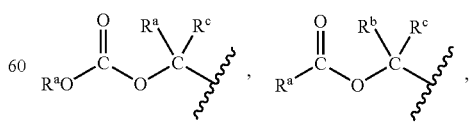

wherein $R^a$, $R^b$ and $R^c$ are H, alkyl, aryl or arylalkyl;
provided that $R^aO$ cannot be HO,
or $R^4$ is

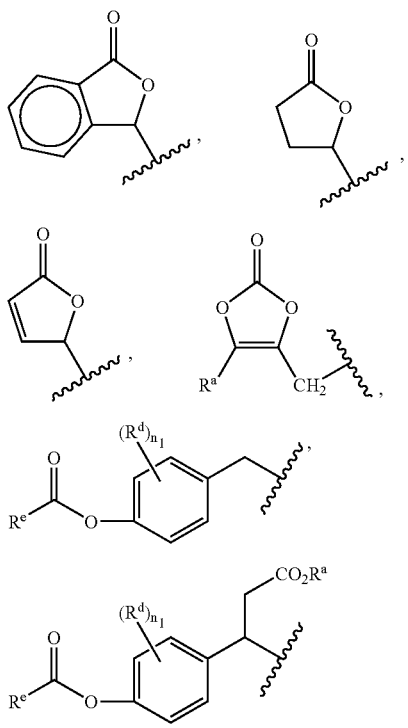

wherein $R^a$ is H, alkyl, arylalkyl or aryl; $R^d$ is H, alkyl, halogen or ailkoxy, $R^e$ is alkyl, aryl, arylalkyl or alkoxyl, and $n_1$ is 0, 1 or 2.

11. The compound as defined in claim 1 having the structure

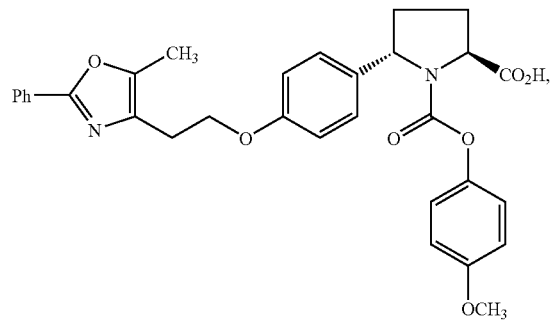

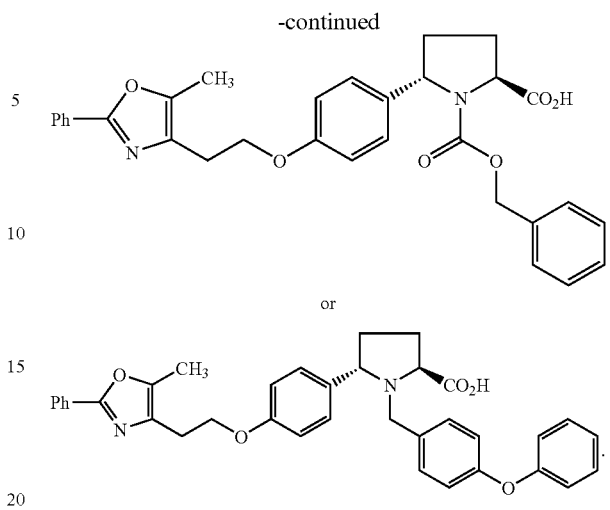

12. A pharmaceutical composition comprising a compound as defined in claim 1 and a pharmaceutically acceptable carrier therefor.

13. A method for lowering blood glucose levels which comprises administering to a patient in need of treatment a therapeutically effective amount of a compound as defined in claim 1.

14. A method for treating diabetes which comprises administering to a patient in need of treatment a therapeutically effective amount of a compound as defined in claim 1.

15. A method for treating a premalignant disease, an early malignant disease, a malignant disease, or a dysplastic disease, which comprises administering to a patient in need of treatment a therapeutically effective amount of a compound as defined in claim 1, wherein the disease is a tumor of the breast, prostate, colon, ovaries, stomach or lung.

16. A method for treating irritable bowel syndrome, Crohn's disease, gastric ulceritis or osteoporosis, or psoriasis, which comprises administering to a mammalian species in need of treatment a therapeutically effective amount of a compound as defined in claim 1.

17. The method as defined in claim 15 wherein the disease is ductal carcinoma in situ of the breast, lobular carcinoma in situ of the breast, fibroadenoma of the breast, or prostatic intraepithelial neoplasia.

* * * * *

UNITED STATES PATENT AND TRADEMARK OFFICE
CERTIFICATE OF CORRECTION

PATENT NO.      : 7,105,556 B2
APPLICATION NO. : 10/153342
DATED           : September 12, 2006
INVENTOR(S)     : Peter T. Cheng, Yoon Jeon and Wei Wang It is certified that error appears in the above-identified patent and that said Letters Patent is hereby corrected as shown below:

Claim 1, column 63, line 50, replace the structure with the following structure

--

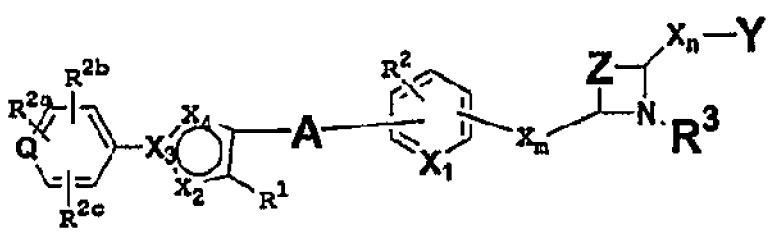

--

Claim 1, column 64, line 37, replace "aryithiocarbonyl" with --arylthiocarbonyl--

Claim 1, column 64, lines 39 and 40, replace "aryiheteroarylalkyl" with --arylheteroarylalkyl--

Claim 1, column 64, lines 43 and 44, replace "arylalkoxycarbonyiheteroarylalkyl" with --arylalkoxycarbonylheteroarylalkyl--

Claim 10, column 65, line 63, replace "ailkynylene" with --alkynylene--

Claim 10, column 66, line 13, replace "ammo" with --amino--

Claim 10, column 66, line 30, replace "aryiheteroarylalkyl" with --arylheteroarylalkyl--

Claim 10, column 66, line 38, replace "aryithiocarbonyl" with --arylthiocarbonyl--

Claim 10, column 66, line 40 and 41, replace "aryiheteroarylalkyl-" with --arylheteroarylalkyl--

Claim 10, column 66, line 44 and 45, replace "arylalkoxycarbonyiheteroarylalkyl" with --arylalkoxycarbonylheteroarylalkyl--

Claim 10, column 66, line 46, replace "arylcarbonyiheteroarylalkyl" with --arylcarbonylheteroarylalkyl--

UNITED STATES PATENT AND TRADEMARK OFFICE
CERTIFICATE OF CORRECTION

PATENT NO. : 7,105,556 B2
APPLICATION NO. : 10/153342
DATED : September 12, 2006
INVENTOR(S) : Peter T. Cheng, Yoon Jeon and Wei Wang It is certified that error appears in the above-identified patent and that said Letters Patent is hereby corrected as shown below:

Claim 10, column 67, line 33, replace "ailkoxy" with --alkoxy--

Signed and Sealed this

Seventh Day of August, 2007

JON W. DUDAS
*Director of the United States Patent and Trademark Office*